US008124775B2

(12) United States Patent
Bischoff et al.

(10) Patent No.: US 8,124,775 B2
(45) Date of Patent: Feb. 28, 2012

(54) CHEMICAL COMPOUND AND ITS USE

(75) Inventors: Hilmar Bischoff, Wuppertal (DE);
Heike Gielen-Haertwig, Monheim
(DE); Volkhart Li, Velbert (DE);
Carsten Schmeck, Oberhausen (DE);
Michael Thutewohl, Buchs (CH);
Alexandros Vakalopoulos, Hilden (DE);
Olaf Weber, Wülfrath (DE); Martina Wuttke, Wuppertal (DE)

(73) Assignee: Bayer Pharma Aktiengesellschaft (DE)

( * ) Notice: Subject to any disclaimer, the term of this patent is extended or adjusted under 35 U.S.C. 154(b) by 750 days.

(21) Appl. No.: 11/793,482

(22) PCT Filed: Dec. 15, 2005

(86) PCT No.: PCT/EP2005/013490
§ 371 (c)(1),
(2), (4) Date: Jan. 16, 2008

(87) PCT Pub. No.: WO2006/063828
PCT Pub. Date: Jun. 22, 2006

(65) Prior Publication Data
US 2008/0255068 A1    Oct. 16, 2008

(30) Foreign Application Priority Data

Dec. 18, 2004  (DE) .................. 10 2004 060 997
Dec. 18, 2004  (DE) .................. 10 2004 061 000

(51) Int. Cl.
*C07D 215/38* (2006.01)
(52) U.S. Cl. ...................... 546/168; 546/167
(58) Field of Classification Search .......... 546/167, 546/168; 514/311
See application file for complete search history.

(56) References Cited

U.S. PATENT DOCUMENTS

| | | | |
|---|---|---|---|
| 5,925,645 A | 7/1999 | Schmidt et al. | |
| 5,932,587 A | 8/1999 | Schmeck et al. | |
| 6,063,788 A | 5/2000 | Brandes et al. | |
| 6,069,148 A * | 5/2000 | Schmidt et al. | 514/277 |
| 6,121,330 A | 9/2000 | Muller-Gliemann et al. | |
| 6,127,383 A | 10/2000 | Schmidt et al. | |
| 6,207,671 B1 | 3/2001 | Schmidt et al. | |
| 6,291,477 B1 * | 9/2001 | Schmidt et al. | 514/311 |
| 6,387,929 B1 | 5/2002 | Stoltefuss et al. | |
| 6,562,976 B2 * | 5/2003 | Schmidt et al. | 546/168 |
| 6,586,613 B1 | 7/2003 | Brandes et al. | 556/449 |
| 6,897,317 B2 * | 5/2005 | Schmidt et al. | 546/167 |
| 6,958,346 B2 | 10/2005 | Stoltefuss et al. | |
| 7,192,971 B2 | 3/2007 | Stoltefuss et al. | |
| 2002/0042515 A1 | 4/2002 | Schmidt et al. | |
| 2005/0043341 A1 | 2/2005 | Gielen et al. | 514/278 |
| 2006/0247303 A1 | 11/2006 | Bischoff et al. | |
| 2008/0194609 A1 * | 8/2008 | Bischoff et al. | 514/278 |

FOREIGN PATENT DOCUMENTS

| | | |
|---|---|---|
| EP | 818448 A1 | 1/1998 |
| WO | 199839299 A1 | 9/1998 |
| WO | 9915504 | 1/1999 |
| WO | 9914174 | 3/1999 |
| WO | WO-99/14215 A1 | 3/1999 |
| WO | 200109144 A1 | 2/2001 |
| WO | 03028727 | 4/2003 |

OTHER PUBLICATIONS

P. A. McCarthy: "New Approaches to Atherosclerosis: An Overview," Medicinal Research Reviews, vol. 13, No. 2, 1993, pp. 139-159.
P. J. Barter et al.: "High Density Lipoproteins and Coronary Heart Disease," Atherosclerosis, vol. 121, 1996, pp. 1-12.
A. R. Tall: "Plasma Cholesteryl Ester Transfer Protein," Journal of Lipid Research, vol. .34, 1993, pp. 1255-1274.
T. L. Swenson et al.: "Mechanism of Cholesteryl Ester Transfer Protein Inhibition by a Neutralizing Monoclonal Antibody and Mapping of the Monoclonal Antibody Epitope," Teh Journal of Biological Chemistry, vol. 264, No. 24, Aug. 25, 1989, pp. 14318-14326.
Third Report of the National Cholesterol Education Program (NCEP) Expert Panel on Detection, Evaluation, and Treatment of High Blood Cholesterol in Adults (Adult Treatment Panel III) Final Report, Circulation 2002, 106; 3143.
C. R. Sirtori: "New Targets for Lipid Lowering and Atherosclerosis Prevention," Pharmac. Ther. vol. 67, No. 3, 1995, pp. 433-447.
C.L. Bisgaier et al., Use of Fluorescent Cholestertyl Ester Microemulsions in Cholesteryl Ester Transfer Proetein Assays, Journal of Lipid Research, 1993,vol. 34, pp. 1625-1634.
A. Gotti et al., Rearrangement of Isoxazoline-5-Spiro Derivatives Part 7 Thermal Rearrangement of 4,5-Dihydro and Tetrahydroisoxazole-5-Spirocyclobutanes to Azepin-4-one Derivatives, Tetrahedron, 1992, vol. 48, No. 25, pp. 5283-5300.
F. Seye-Mandavi et al., Reactivity Enhancement through Strain and Electronic Effects—Heterocyclopropylidenacetates as Powerful Michael Receptors, Tetradedron Letters, 1986, vol. 27, No. 41, pp. 6185-6188.
A. Weichert et al, Palladium (0) Catalyzed Cross Coupling Reactions of Hindered Double Activated Aryl Halides with Organozinc Reagents—The Effect of Copper (1) Cocatalysis, Syunlett, May 1996, pp. 473-474.
M. Ueda et al., A Large Accelerating Effect of Tri(tert-butyl)phosphine in the Rhodium-Catalyzed Addiotn of Arylboronic Acids to Aldehydes, J. Org. Chem., 2000, vol. 65, pp. 4450-4452.
J. Hassan et al., Aryl-Aryl Bond Formation One Century after the Discovery of the Ullmann Reaction, Chem. Rev., 2002, vol. 102, pp. 1359-1469.
L. Xie et al., Anti-AIDS Agents 42 Synthesis and Anti-HIV Activity of Disubstituted (3'R, 4'R)-3', 4'-Di-O-(S)-camphanoy1-(+)-cis-khellactone Analogues, J. Med. Chem. 2001, vol. 44, pp. 664-671.
J. Dinchuk et al., Remodeling of Lipoproteins in Transgenic Mice Expressing Human Cholesteryl Ester Transfer Protein, Biochimica et Biophysica Acta, 1995, vol. 1255, pp. 301-310.
Paulsen, et al., Fluorine-Substitution in Cholesteryl Ester Transfer Protein Inhibitors (CETP-Inhibitors)—Biology, chemistry, SAR and Properties, CHIMIA, 2004, 58:3, pp. 123-127.
U.S. Appl. No. 12/225,211, filed Jul. 6, 2009.

* cited by examiner

*Primary Examiner* — D M Seaman
(74) *Attorney, Agent, or Firm* — Jonathan R. Harris; Karen B. King

(57) ABSTRACT

The present application relates to a novel tetrahydroquinoline derivative, to a process for its preparation, to its use on its own or in combination for treating and/or preventing diseases and to its use for preparing medicaments, in particular as an inhibitor of the cholesterol ester transfer protein (CETP) for the treatment and/or prevention of cardiovascular disorders, in particular hypolipoproteinaemias, dyslipidaemias, hypertriglyceridaemias, hyperlipidaemias, hypercholesterolaemias and arteriosclerosis.

9 Claims, No Drawings

CHEMICAL COMPOUND AND ITS USE

The present application relates to a novel tetrahydroquinoline derivative, to a process for this preparation, to its use on its own or in combination for treating and/or preventing diseases and to its use for preparing medicaments, in particular as an inhibitor of the cholesterol ester transfer protein (CETP) for the treatment and/or prevention of cardiovascular disorders, in particular hypolipoproteinaemias, dyslipidaemias, hypertriglyceridaemias, hyperlipidaemias, hypercholesterolaemias and arteriosclerosis.

Coronary heart disease caused by arteriosclerosis is one of the main causes of death in modern society. In a large number of studies, it was shown that low plasma concentrations of HDL cholesterol are an important risk factor for the development of arteriosclerosis [Barter and Rye, *Atherosclerosis* 121, 1-12 (1996)]. HDL (high density lipoprotein), in addition to LDL (low density lipoprotein) and VLDL (very low density lipoprotein), is a class of lipoproteins whose most important function is the transport of lipids, such as, for example, cholesterol, cholesterol esters, triglycerides, fatty acids or phospholipids, in the blood. High LDL cholesterol concentrations (>160 mg/dl) and low HDL cholesterol concentrations (<40 mg/dl) contribute substantially to the development of arteriosclerosis [ATP III Guidelines, Report of the NCEP Expert Panel]. In addition to coronary heart disease, unfavourable HDL/LDL ratios also promote the development of peripheral vascular disorders and stroke. Accordingly, novel methods for elevating HDL cholesterol in the plasma are a therapeutically useful advance in the prevention and treatment of arteriosclerosis and the disorders associated therewith.

Cholesterol ester transfer protein (CETP) mediates the exchange of cholesterol esters and triglycerides between the different lipoproteins in the blood [Tall, *J. Lipid Res.* 34, 1255-74 (1993)]. Of particular importance here is the transfer of cholesterol esters from HDL to LDL, which results in a reduction of the plasma HDL cholesterol concentration. Accordingly, inhibition of CETP should result in elevated plasma HDL cholesterol concentrations and a reduction of the plasma LDL cholesterol concentrations and thus in a therapeutically useful effect on the lipid profile in the plasma [McCarthy, *Medicinal Res. Rev.* 13, 139-59 (1993); Sitori, *Pharmac. Ther.* 67, 443-47 (1995); Swenson, *J. Biol. Chem.* 264, 14318 (1989)].

Tetrahydroquinolines having pharmacological activity are known from EP-A-818 448, WO 99/14215, WO 99/15504 and WO 03/028727. Substituted tetrahydronaphthalenes having pharmacological activity are known from WO 99/14174.

It is an object of the present invention to provide novel substances for controlling disorders, in particular cardiovascular disorders, which substances have an improved therapeutic profile.

The present invention provides the compounds of the structural formula (I)

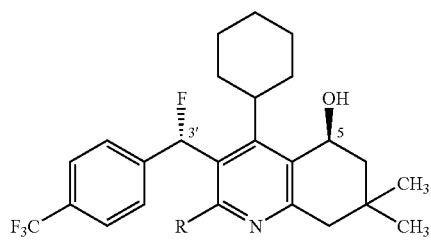

in which R represents cyclopentyl or isopropyl, and their salts, solvates and solvates of the salts.

The present invention provides in particular the compound having the systematic name (5S)-4-cyclohexyl-2-cyclopentyl-3-{(S)-fluoro[4-(trifluoromethyl)phenyl]methyl}-7,7-dimethyl-5,6,7,8-tetrahydroquinolin-5-ol and the structural formula (Ia)

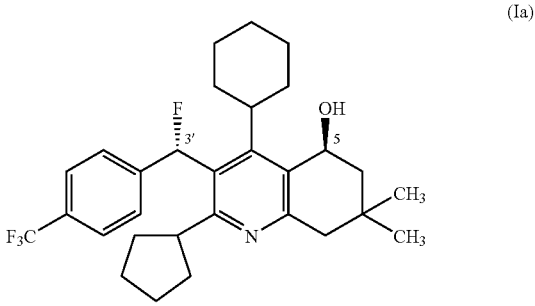

and its salts, solvates and solvates of the salts.

The present invention in particular also provides the compound having the systematic name (5S)-4-cyclopentyl-3-{(S)-fluoro[4-(trifluoromethyl)phenyl]methyl}-2-isopropyl-7,7-dimethyl-5,6,7,8-tetrahydroquinolin-5-ol and the structural formula (Ib)

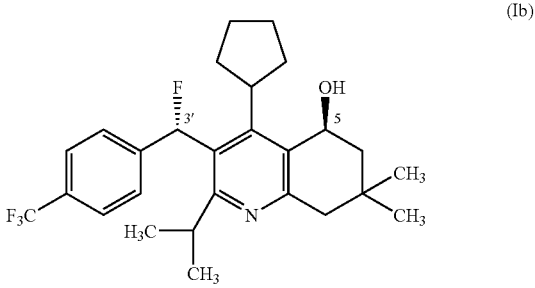

and its salts, solvates and solvates of the salts.

Hereinbelow, the compounds of the formula (I), (Ia) and (Ib) are referred to in the singular as "compound according to the invention"; however, the description relates to both compounds.

The compound according to the invention can also be present in other stereoisomeric forms (enantiomers, diastereomers). The present invention comprises all enantiomers, diastereomers and their respective mixtures. From such mixtures of enantiomers and/or diastereomers, the stereoisomerically uniform components can be isolated in a known manner. Preferred is the S-configuration at C-5 and at C-3' shown in formula (I).

In the context of the present invention, preferred salts are physiologically acceptable salts of the compound according to the invention. However, salts which for their part are unsuitable for pharmaceutical applications but which can be used, for example, for isolating or purifying the compound according to the invention are also included.

Physiologically acceptable salts of the compound according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compound according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compound according to the invention which, in solid or liquid state, form a complex by coordination with solvent molecules. Hydrates are a special form of solvates where the coordination is with water. In the context of the present invention, preferred solvates are hydrates.

Moreover, the present invention also includes prodrugs of the compound according to the invention. The term "prodrugs" includes compounds which for their part may be biologically active or inactive but are converted (for example metabolically or hydrolytically) into the compound according to the invention during their residence time in the body.

In the context of the invention, $(C_1-C_4)$ alkyl represents a straight-chain or branched alkyl radical having 1 to 4 carbon atoms. The following radicals may be mentioned by way of example and by way of preference: methyl, ethyl, n-propyl, isopropyl, n-butyl, isobutyl, sec-butyl and tert-butyl.

The invention also provides a process for preparing the compound of the formula (Ia) according to the invention, characterized in that the compound of the formula (IIa)

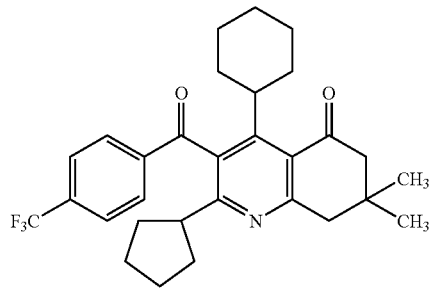

(IIa)

is initially, by asymmetric reduction, converted into the compound of the formula (IIIa)

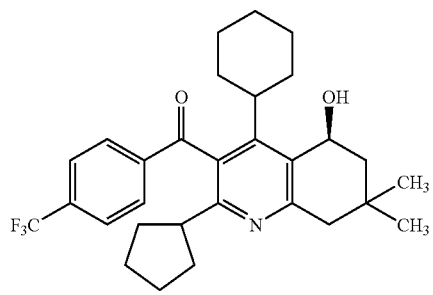

(IIIa)

which is then either
[A] by introduction of a hydroxyl protective group reacted to give a compound of the formula (IVa)

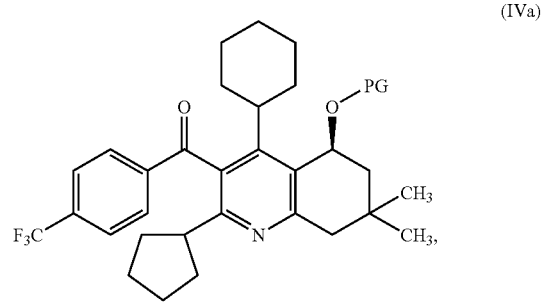

(IVa)

in which
PG represents a hydroxyl protective group, preferably a radical of the formula $—SiR^1R^2R^3$, in which
$R^1$, $R^2$ and $R^3$ are identical or different and represent $(C_1-C_4)$ alkyl,
and then, by diastereoselective reduction, converted into a compound of the formula (Va)

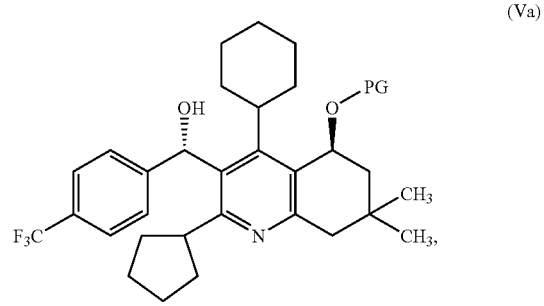

(Va)

in which PG is as defined above,
or in the reverse order of the reaction sequence
[B] initially reduced diastereoselectively to give the compound of the formula (VIa)

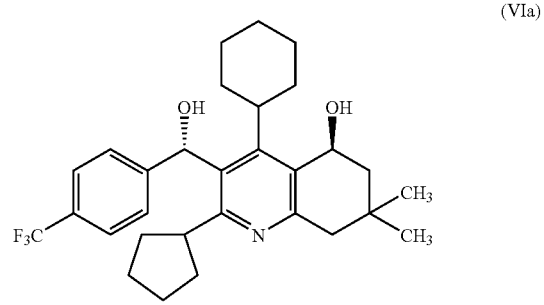

(VIa)

which is then, by regioselective introduction of the hydroxyl protective group PG, converted into a compound of the formula (Va), the compound of the formula (Va) is then, using a fluorinating agent, reacted to give a compound of the formula (VIIa)

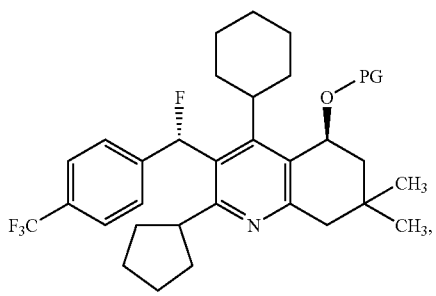

(VIIa)

in which PG is as defined above,
and the hydroxyl protective group PG is then cleaved off by customary methods giving the compound of the formula (Ia)
and the compound of the formula (Ia) is, if appropriate, converted with the appropriate (i) solvents and/or (ii) bases and/or acids into its solvates, salts and/or solvates of the salts.

The compound of the formula (IIa) can be prepared by reacting the compounds of the formulae (VIII), (IX) and (Xa)

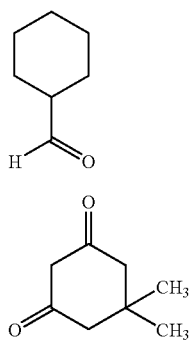

(VIII)

(IX)

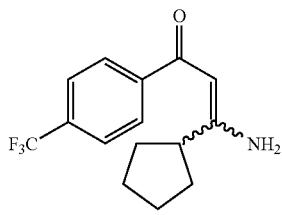

(Xa)

in a 3-component reaction in the presence of a protic acid or Lewis acid with one another to give the compound of the formula (XIa)

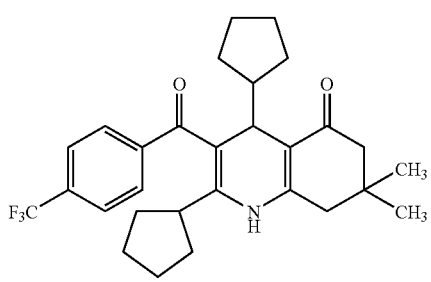

(XIa)

and then oxidizing this compound to the compound of the formula (IIa).

The invention furthermore provides a process for preparing the compound of the formula (Ib) according to the invention, characterized in that the compound of the formula (IIb)

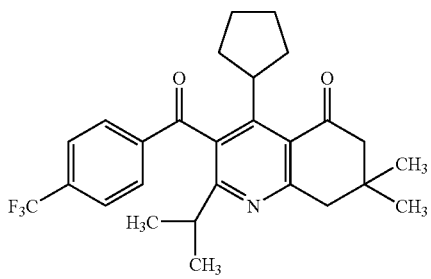

(IIb)

is initially, by asymmetric reduction, converted into the compound of the formula (IIIb)

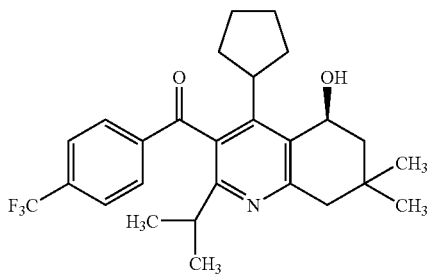

(IIIb)

which is then either

[A] by introduction of a hydroxyl protective group reacted to give a compound of the formula (IVb)

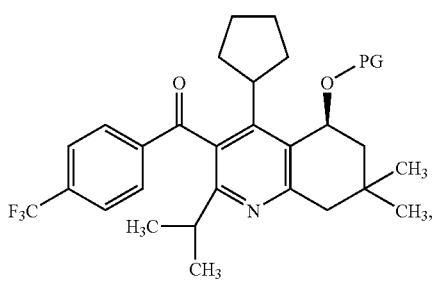

(IVb)

in which
PG represents a hydroxyl protective group, preferably a radical of the formula —SiR$^1$R$^2$R$^3$, in which
R$^1$, R$^2$ and R$^3$ are identical or different and represent (C$_1$-C$_4$) alkyl,
and then, by diastereoselective reduction, converted into a compound of the formula (Vb)

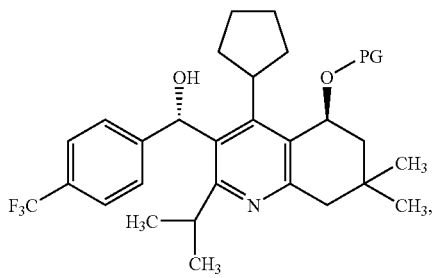
(Vb)

in which PG is as defined above, or in the reverse order of the reaction sequence

[B] initially reduced diastereoselectively to give the compound of the formula (VIb)

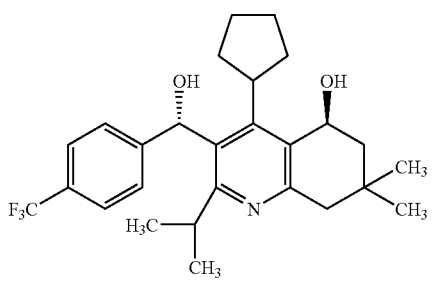
(VIb)

which is then, by regioselective introduction of the hydroxyl protective group PG, converted into a compound of the formula (Vb), the compound of the formula (Vb) is then, using a fluorinating agent, reacted to give a compound of the formula (VIIb)

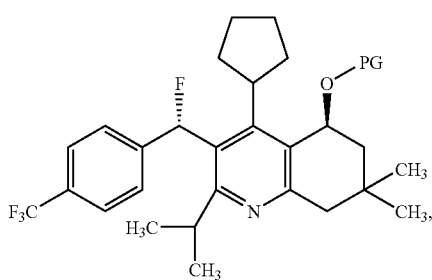
(VIIb)

in which PG is as defined above, and the hydroxyl protective group PG is then cleaved off by customary methods giving the compound of the formula (Ib)

and the compound of the formula (Ib) is, if appropriate, converted with the appropriate (i) solvents and/or (ii) bases or acids into its solvates, salts and/or solvates of the salts.

The compound of the formula (IIb) can be prepared by reacting the compounds of the formulae (VIII), (IX) and (Xb)

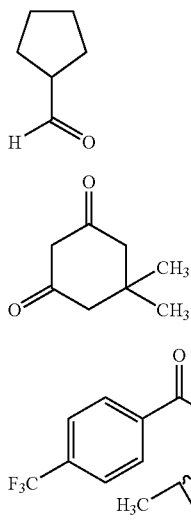

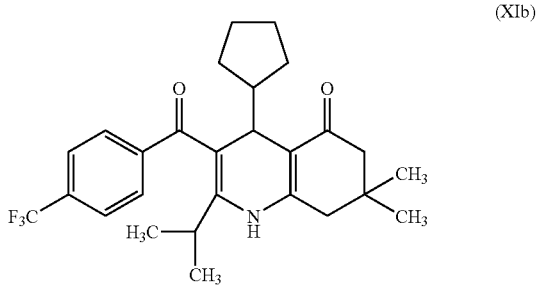

in a 3-component reaction in the presence of a protic acid or Lewis acid with one another to give the compound of the formula (XIb)

(XIb)

and then oxidizing this compound to give the compound of the formula (IIb).

Compounds of the formulae (VIII), (IX) and (Xa) and (Xb) are commercially obtainable, known from the literature or can be prepared analogously to processes known from the literature (cf. also WO 99/14215 and WO 03/028727).

Suitable inert solvents for the individual process steps are, for example, ethers, such as diethyl ether, diisopropyl ether, dioxane, tetrahydrofuran, glycol dimethyl ether or diethylene glycol dimethyl ether, hydrocarbons, such as benzene, toluene, xylene, hexane, cyclohexane or mineral oil fractions, or halogenated hydrocarbons, such as dichloromethane, trichloromethane, carbon tetrachloride, 1,2-dichloroethane, trichloroethylene or chlorobenzene. It is also possible to use mixtures of the solvents mentioned.

The reductions in process steps (II)→(III), (IV)→(V) and (III)→(VI) are generally carried out using reducing agents suitable for reducing ketones to hydroxyl compounds. These include, in particular, complex aluminium hydrides or borohydrides, such as, for example, lithium hydride, sodium hydride, potassium hydride, zinc borohydride, lithium aluminium hydride, diisobutylaluminium hydride (DIBAH), sodium bis-(2-methoxyethoxy)aluminium dihydride, lithium trialkylborohydrides or lithium trialkoxyaluminium hydrides, or borane complexes, such as, for example, borane tetrahydrofuran, borane dimethyl sulphide or borane N,N-diethylaniline complex.

The asymmetric reduction in process step (II)→(III) is carried out in the presence of catalytic amounts (0.01 to 0.3 mol equivalents) of enantiomerically pure (1R,2S)-1-aminoindan-2-ol as chiral inductor. The reducing agent which is preferably used for this purpose is borane N,N-diethylaniline complex. The reaction is generally carried out in one of the ethers listed above or in toluene, preferably in tetrahydrofuran, in a temperature range of from −80° C. to +50° C., preferably from 0° C. to +30° C.

The reducing agent used for the reductions (IV)→(V) and (III)→(VI) is preferably lithium aluminium hydride or DIBAH. The reactions are generally carried out in one of the ethers listed above or in toluene, preferably in tetrahydrofuran or toluene, in a temperature range of from −80° C. to +50° C., in the case of lithium aluminium hydride preferably from 0° C. to +30° C. and in the case of DIBAH preferably from −80° C. to +30° C.

A preferred hydroxyl protective group for process steps (III)→(IV) or (VI)→(V) is a silyl group, such as, for example, trimethylsilyl, triethylsilyl, triisopropylsilyl or tert-butyldimethylsilyl. Particular preference is given to tert-butyldimethylsilyl. The silyl group is generally introduced in one of the abovementioned hydrocarbons, halogenated hydrocarbons, ethers or in dimethylformamide as solvent, in the presence of a base, such as, for example, triethylamine, N,N-diisopropylethylamine, pyridine, 2,6-lutidine or 4-N,N-dimethylaminopyridine (DMAP).

In process step (III)→(IV), the silylating agent used is preferably tert-butyldimethylsilyl trifluoromethanesulphonate in combination with 2,6-lutidine as base. The reaction is preferably carried out in dichloromethane or toluene, in a temperature range of from −40° C. to +40° C., preferably from −20° C. to +30° C.

In process step (VI)→(V), the silylating agent used is preferably tert-butyldimethylsilyl chloride in combination with triethylamine and DMAP as bases. The reaction is preferably carried out in dimethylformamide, in a temperature range of from 0° C. to +100° C., preferably from +20° C. to +80° C.

The fluorination in process step (VI)→(VII) is generally carried out in one of the abovementioned hydrocarbons or halogenated hydrocarbons or in acetonitrile, preferably in toluene or dichloromethane, using diethylaminosulphur trifluoride (DAST) or morpholino-sulphur trifluoride as fluorinating agent. The reaction is generally carried out in a temperature range of from −80° C. to +40° C., preferably from −60° C. to +20° C.

Removal of a silyl protective group in process step (VII)→(I) is generally carried out with the aid of acids, such as, for example, hydrochloric acid or trifluoroacetic acid, or with the aid of fluorides, such as, for example, hydrogen fluoride or tetrabutylammonium fluoride (TBAF). Suitable inert solvents are the abovementioned ethers, alcohols, such as methanol or ethanol, or mixtures of the solvents mentioned. The removal is preferably carried out using TBAF in tetrahydrofuran as solvent. The reaction is generally carried out in a temperature range of from −20° C. to +60° C., preferably from 0° C. to +30° C.

The condensation reaction (VIII)+(IX)+(X)→(XI) is generally carried out in one of the abovementioned ethers, in alcohols, such as methanol, ethanol, n-propanol or isopropanol, in acetonitrile or in mixtures of the solvents mentioned. Preference is given to using diisopropyl ether.

Protic acids suitable for this process step are, in general, organic acids, such as, for example, acetic acid, trifluoroacetic acid, oxalic acid or para-toluenesulphonic acid, or inorganic acids, such as, for example, hydrochloric acid, sulphuric acid, or phosphoric acid. Also suitable are Lewis acids, such as, for example, aluminium chloride or zinc chloride. Preference is given to trifluoroacetic acid.

In general, the reaction is carried out in a temperature range of from 0° C. to +120° C., preferably from +20° C. to +80° C.

The oxidation (dehydrogenation) in process step (XI)→(II) is generally carried out in one of the halogenated hydrocarbons listed above, or, if appropriate, in alcohols, such as methanol or ethanol, in acetonitrile or in water. Suitable oxidizing agents are, for example, nitric acid, cerium(IV) ammonium nitrate, 2,3-dichloro-5,6-dicyano-1,4-benzoquinone (DDQ), pyridinium chlorochromate (PCC), osmium tetroxide, manganese dioxide or a catalytic dehydrogenation using platinum dioxide or palladium-on-carbon. Preference is given to an oxidation using DDQ in dichloromethane as solvent. The oxidation is generally carried out in a temperature range of from −50° C. to +100° C., preferably from 0° C. to +40° C.

The individual process steps can be carried out at atmospheric, elevated or reduced pressure (for example from 0.5 to 5 bar). In general, the process steps are carried out at atmospheric pressure.

The preparation of the compound according to the invention can be illustrated by the synthesis scheme below:

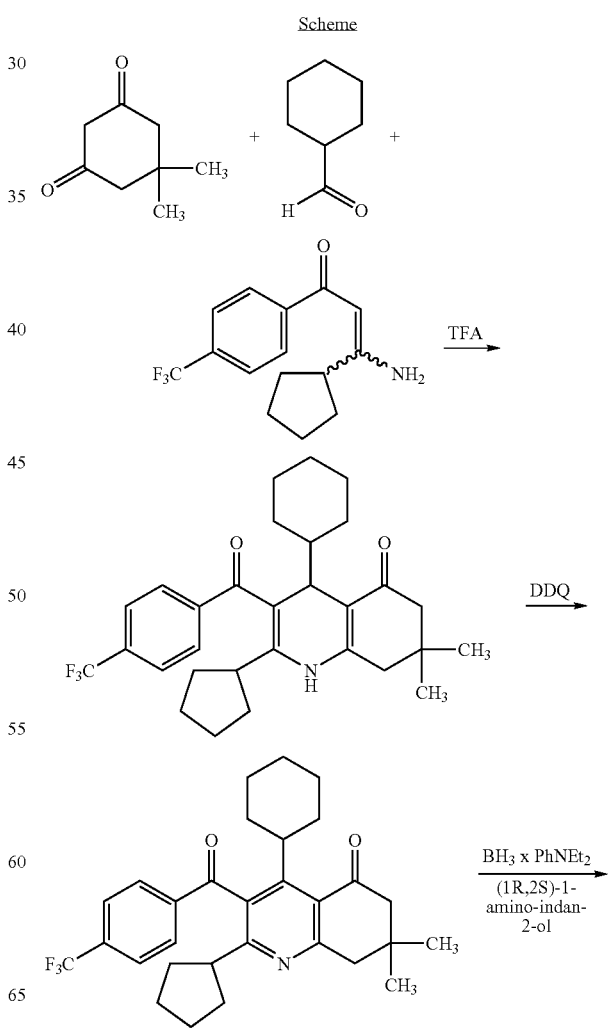

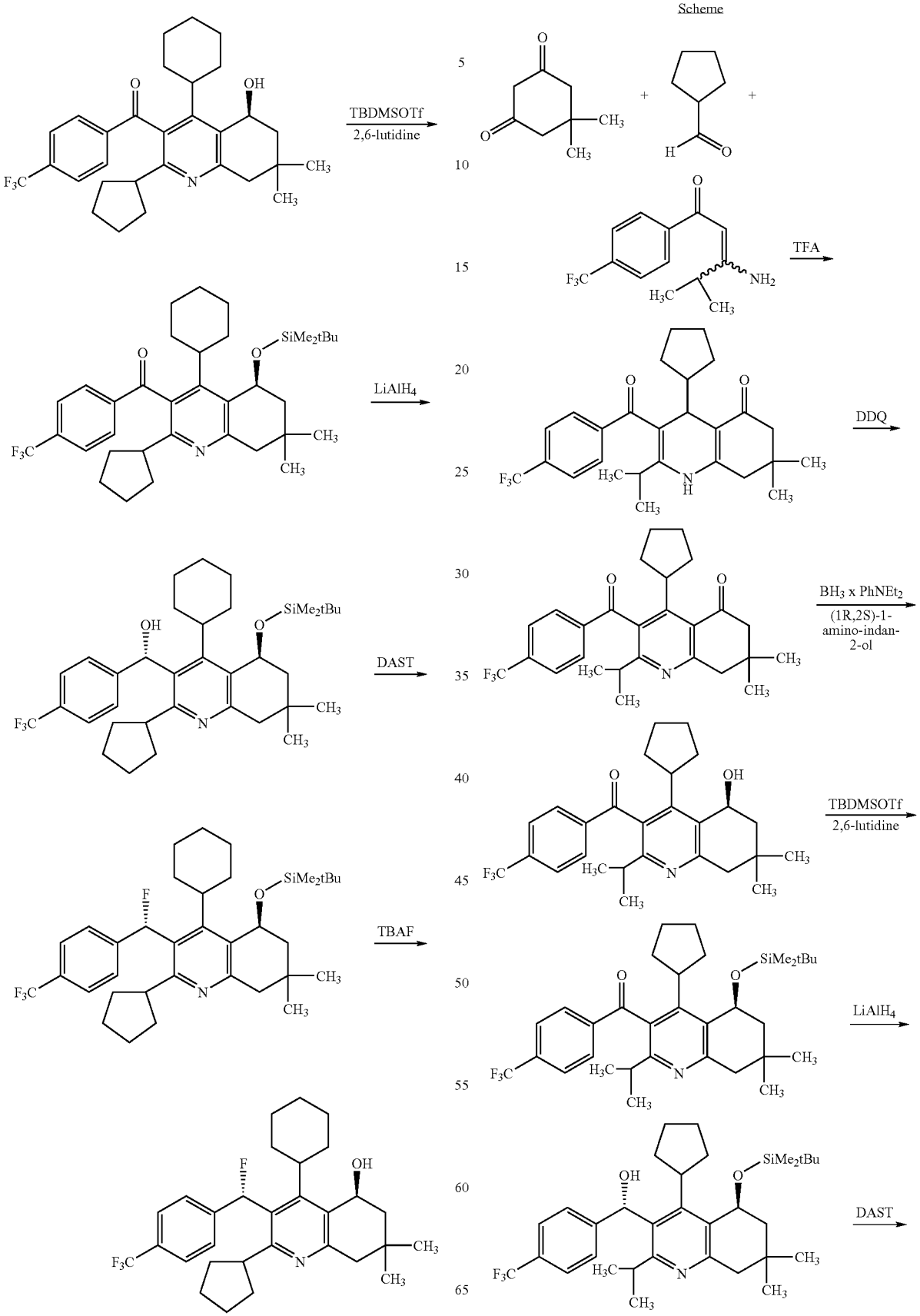

-continued

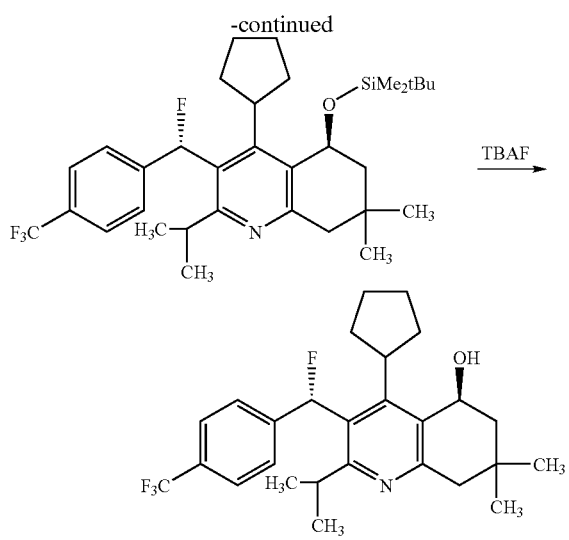

[abbreviations: tBu=tert-butyl; DAST=dimethylaminosulphur trifluoride; DDQ=2,3-dichloro-5,6-dicyano-1,4-benzoquinone; Et=ethyl; Me=methyl; Ph=phenyl; TBAF=tetrabutylammonium fluoride; TBDMSOTf=tert-butyldimethylsilyl trifluoromethanesulphonate; TFA=trifluoroacetic acid].

The compound according to the invention has an unforeseeable useful pharmacological activity spectrum. Accordingly, it is suitable for use as a medicinally active compound for the treatment and/or prophylaxis of diseases in humans and animals.

The compound according to the invention opens up a further treatment alternative and represents an advance of pharmacy. In comparison to the known and previously employed preparations, the compound according to the invention shows an improved spectrum of action.

It is preferably distinguished by great specificity, good tolerability and fewer side-effects, and also a reduced toxicity, in particular in the cardiovascular area and in the liver area.

An advantage of the compound according to the invention is its high activity in human plasma. A further advantage of the compound according to the invention is a reduced potential for interactions with metabolizing enzymes, in particular the cytochrome P450 enzymes and especially the cytochrome P450 3A4 enzyme. In addition, the compound according to the invention has a reduced tendency to deposit itself in fatty tissues.

The compound of the formula (I) according to the invention has useful pharmacological properties and can be used for the prevention and treatment of disorders. The compound according to the invention is in particular a highly effective inhibitor of the cholesterol ester transfer protein (CETP) and stimulates reverse cholesterol transport. It elevates the HDL cholesterol concentration in the blood. The compound according to the invention is particularly suitable for the treatment and for primary or secondary prevention of coronary heart disease, for example myocardial infarction. In addition, the compound according to the invention can be used for the treatment and prevention of arteriosclerosis, restenosis, strokes and Alzheimer's disease. Moreover, the compound according to the invention can also be used for the treatment and prevention of hypolipoproteinaemias, dyslipidaemias, hypertriglyceridaemias, hyperlipidaemias, hypercholesterolaemias, adiposity, obesity, pancreatitis, insulin-dependent and non-insulin-dependent diabetes, diabetic sequelae such as, for example, retinopathy, nephropathy and neuropathy, of combined hyperlipidaemias and of the metabolic syndrome.

The pharmacological action of the compound according to the invention can be determined using the CETP inhibition tests described below.

The present invention furthermore provides the use of the compound according to the invention for the treatment and/or prevention of disorders, in particular the disorders mentioned above.

The present invention furthermore provides the use of the compound according to the invention for preparing a medicament for the treatment and/or prevention of disorders, in particular the disorders mentioned above.

The present invention furthermore provides a method for the treatment and/or prevention of disorders, in particular the disorders mentioned above, using an effective amount of the compound according to the invention.

The present invention furthermore provides medicaments comprising the compound according to the invention and one or more further active compounds, for the treatment and/or prevention of disorders. Active compounds suitable for combinations are, by way of example and by way of preference:
antidiabetics,
substances having antithrombotic action,
hypotensive substances,
lipid metabolism-modifying substances,
anti-inflammatory substances,
substances which stabilize arteriosclerotic plaque.

The compound of the formula (I) according to the invention can preferably be combined with one or more
antidiabetics mentioned in the Roten Liste [red list] 2002/II, chapter 12,
agents having antithrombotic action, by way of example and by way of preference from the group of the platelet aggregation inhibitors or the anticoagulants,
hypotensive agents, by way of example and by way of preference from the group of the calcium antagonists, angiotensin AII antagonists, ACE inhibitors beta blockers, phosphodiesterase inhibitors, stimulators of soluble guanylate cyclase, cGMP enhancers and diuretics, and/or
active compounds which modify lipid metabolism, by way of example and by way of preference from the group of the thyroid receptor agonists, the cholesterol synthase inhibitors, such as HMG-CoA reductase inhibitors, squalene synthase inhibitors, squalene epoxidase inhibitors or oxidosqualene cyclase inhibitors, the ACAT inhibitors, MTP inhibitors, PPAR agonists, fibrates, lipase inhibitors, cholesterol absorption inhibitors, bile acid reabsorption inhibitors, polymeric bile acid adsorbers and the lipoprotein(a) antagonists.

Antidiabetics are to be understood as meaning, by way of example and by way of preference, insulin and insulin derivatives, and also orally effective compounds with hypoglycaemic action.

Here, insulin and insulin derivatives include both insulins of animal, human or biotechnological origin and mixtures thereof.

The orally effective compounds with hypoglycaemic action include, by way of example and by way of preference, sulphonylureas, biguanidines, meglitinide derivatives, oxadiazolidinones, thiazolidinediones, glucosidase inhibitors, glucagon antagonists, GLP-1 agonists, insulin sensitizers, inhibitors of liver enzymes involved in the stimulation of gluconeogenesis and/or glycogenolysis, modulators of glucose uptake and potassium channel openers, such as, for example, those disclosed in WO 97/26265 and WO 99/03861.

In a preferred embodiment of the invention, the compound of the formula (I) is administered in combination with insulin.
·#

In a preferred embodiment of the invention, the compound of the formula (I) is administered in combination with a sulphonylurea, such as, by way of example and by way of preference, tolbutamide, glibenclamide, glimepiride, glipizide or gliclazide.

In a preferred embodiment of the invention, the compound of the formula (I) is administered in combination with a biguanide, such as, by way of example and by way of preference, metformin.

In a preferred embodiment of the invention, the compound of the formula (I) is administered in combination with a meglitinide derivative, such as, by way of example and by way of preference, repaglinide or nateglinide.

In a preferred embodiment of the invention, the compound of the formula (I) is administered in combination with a PPARgamma agonist, for example from the class of the thiazolidinediones, such as, by way of example and by way of preference, pioglitazone or rosiglitazone.

In a preferred embodiment of the invention, the compound of the formula (I) is administered in combination with a mixed PPARalpha/gamma agonist, such as, by way of example and by way of preference, GI-262570 (farglitazar), GW 2331, GW 409544, AVE 8042, AVE 8134, AVE 0847, MK-0767 (KRP-297) or AZ-242.

Agents with antithrombotic action are to be understood as meaning, preferably, compounds from the group of the platelet aggregation inhibitors, such as, by way of example and by way of preference, aspirin, clopidogrel, ticlopidine or dipyridamole, or of the anticoagulants.

In a preferred embodiment of the invention, the compound of the formula (I) is administered in combination with a thrombin inhibitor, such as, by way of example and by way of preference, ximelagatran, melagatran, bivalirudin or clexane.

In a preferred embodiment of the invention, the compound of the formula (I) is administered in combination with a GPIIb/IIIa antagonist, such as, by way of example and by way of preference, tirofiban or abciximab.

In a preferred embodiment of the invention, the compound of the formula (I) is administered in combination with a factor Xa inhibitor, such as, by way of example and by way of preference, DX 9065a, DPC 906, JTV 803 or BAY 59-7939.

In a preferred embodiment of the invention, the compound of the formula (I) is administered in combination with heparin or a low-molecular-weight (LMW) heparin derivative.

In a preferred embodiment of the invention, the compound of the formula (I) is administered in combination with a vitamin K antagonist, such as, by way of example and by way of preference, coumarin.

Hypotensive agents are to be understood as meaning, by way of example and by way of preference, compounds from the group of the calcium antagonists, such as, by way of example and by way of preference, the compounds nifedipine, amlodipine, nitrendipine, nisoldipine, verapamil or diltiazem, of the angiotensin AII antagonists, ACE inhibitors, beta blockers and the diuretics.

In a preferred embodiment of the invention, the compound of the formula (I) is administered in combination with an antagonist of the alpha 1 receptors.

In a preferred embodiment of the invention, the compound of the formula (I) is administered in combination with reserpine, minoxidil, diazoxide, dihydralazine, hydralazine and nitrous oxide-releasing substances, such as, by way of example and by way of preference, glycerol nitrate or sodium nitroprusside.

In a preferred embodiment of the invention, the compound of the formula (I) is administered in combination with an angiotensin AII antagonist, such as, by way of example and by way of preference, losartan, valsartan, candesartan, telmisartan, embusartan, irbesartan, olmesartan, tasosartan or saprisartan.

In a preferred embodiment of the invention, the compound of the formula (I) is administered in combination with an ACE inhibitor, such as, by way of example and by way of preference, enalapril, captopril, ramipril, delapril, fosinopril, quinopril, perindopril or trandolapril.

In a preferred embodiment of the invention, the compound of the formula (I) is administered in combination with a beta blocker, such as, by way of example and by way of preference, propranolol or atenolol.

In a preferred embodiment of the invention, the compound of the formula (I) is administered in combination with a diuretic, such as, by way of example and by way of preference, furosemide.

Lipid metabolism-modifying agents are to be understood as meaning, by way of example and by way of preference, compounds from the group of the thyroid receptor agonists, the cholesterol synthesis inhibitors, such as HMG-CoA reductase inhibitors or squalene synthesis inhibitors, the ACAT inhibitors, MTP inhibitors, PPAR agonists, fibrates, cholesterol absorption inhibitors, bile acid reabsorption inhibitors, lipase inhibitors, polymeric bile acid adsorbers and the lipoprotein(a) antagonists.

In a preferred embodiment of the invention, the compound of the formula (I) is administered in combination with a thyroid receptor agonist, such as, by way of example and by way of preference, D-thyroxine, 3,5,3'-triiodothyronine (T3), CGS 23425 or axitirome (CGS 26214).

In a preferred embodiment of the invention, the compound of the formula (I) is administered in combination with a squalene synthesis inhibitor, such as, by way of example and by way of preference, BMS-188494 or TAK 475.

In a preferred embodiment of the invention, the compound of the formula (I) is administered in combination with an ACAT inhibitor, such as, by way of example and by way of preference, avasimibe, eflucimibe or CS-505.

In a preferred embodiment of the invention, the compound of the formula (I) is administered in combination with a cholesterol absorption inhibitor, such as, by way of example and by way of preference, ezetimibe, tiqueside or pamaqueside.

In a preferred embodiment of the invention, the compound of the formula (I) is administered in combination with a bile acid reabsorbtion inhibitor, such as, by way of example and by way of preference, barixibat, AZD 7508, SC 435, SC 635, S-8921, 264W94 or HM 1453.

In a preferred embodiment of the invention, the compound of the formula (I) is administered in combination with an MTP inhibitor, such as, by way of example and by way of preference, implitapide, BMS-201038 or R-103757.

In a preferred embodiment of the invention, the compound of the formula (I) is administered in combination with a PPARalpha agonist, such as, for example, the fibrates fenofibrate, clofibrate, bezafibrate, ciprofibrate or gemfibrozil, or such as, by way of example and by way of preference, GW 9578, GW 7647, LY-518674 or NS-220.

In a preferred embodiment of the invention, the compound of the formula (I) is administered in combination with a PPARdelta agonist, such as, by way of example and by way of preference, GW 501516.

In a preferred embodiment of the invention, the compound of the formula (I) is administered in combination with a mixed PPARalpha/gamma agonist, such as, by way of example and by way of preference, GI-262570 (farglitazar), GW 2331, GW 409544, AVE 8042, AVE 8134, AVE 0847, MK-0767 (KRP-297) or AZ-242.

In a preferred embodiment of the invention, the compound of the formula (I) is administered in combination with a mixed PPARalpha/gamma/delta agonist, such as, by way of example and by way of preference, MCC-555.

In a preferred embodiment of the invention, the compound of the formula (I) is administered in combination with a lipase inhibitor from the group of the endothelial lipase inhibitors, the pancreatic lipase inhibitors, the gastric lipase inhibitors, the hormone-sensitive lipase inhibitors or the hepatic lipase inhibitors.

In a particularly preferred embodiment of the invention, the compound of the formula (I) is administered in combination with an inhibitor of pancreatic lipase, preferably from the class of the lipstatins, such as, by way of example, orlistat.

In a preferred embodiment of the invention, the compound of the formula (I) is administered in combination with a polymeric bile acid adsorber, such as, by way of example and by way of preference, cholestyramine, colestipol, colesolvam, CholestaGel or colestimide.

In a preferred embodiment of the invention, the compound of the formula (I) is administered in combination with a lipoprotein(a) antagonist, such as, by way of example and by way of preference, gemcabene calcium (CI-1027) or nicotinic acid.

In a preferred embodiment of the invention, the compound of the formula (I) is administered in combination with an antagonist of the niacin receptor, such as, by way of example and by way of preference, niaspan, acipimox or niceritrol.

In a preferred embodiment of the invention, the compound of the formula (I) is administered in combination with an antioxidant, such as, by way of example and by way of preference, probucol, AGI 1067 or Bo 653.

In a preferred embodiment of the invention, the compound of the formula (I) is administered in combination with an LDL receptor inducer, such as, by way of example, lifibrol.

In a preferred embodiment of the invention, the compound of the formula (I) is administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

The present invention also provides combinations of the compound of the formula (I) with substances which reduce the gene expression of HMG-CoA reductase. Such substances may, for example, be inhibitors of HMG-CoA reductase transcription or HMG-CoA reductase translation. Inhibition of HMG-CoA reductase gene expression may be effected, for example, by inhibiting S1P (Site-1) protease, or by lowering the SREBP (sterol receptor binding protein) concentration.

The present invention also provides combinations of the compound of the formula (I) with substances which may have anti-inflammatory action and/or stabilize arteriosclerotic plaque. Such substances may, for example, be active compounds from the class of the NSAIDs, the PAF-AH antagonists or the chemokine receptor antagonists, such as, by way of example, IL-8 receptor antagonists or MCP-1 antagonists.

The active compound combinations according to the invention have useful pharmacological properties and can be used for the prophylaxis and treatment of disorders. The active compound combinations according to the invention are particularly suitable for the treatment and for the primary or secondary prevention of coronary heart disease, for example of miocardial infarction. Additionally, they can be used for the treatment and prevention of arteriosclerosis, restenosis, stroke and Alzheimer's disease. In addition, the active compound combinations mentioned can also be employed for the treatment and prevention of hypolipoproteinaemias, dyslipidaemias, hypertriglyceridaemias, hyperlipidaemias, hypercholesterolaemias, adiposity, obesity, pancreatitis, insulin-dependent and non-insulin-dependent diabetes, diabetic sequelae, such as, for example, retinopathy, nephropathy and neuropathy, of combined hyperlipidemias and of the metabolic syndrome. Furthermore, the active compound combinations according to the invention are suitable for treating hypertension, heart failure, angina pectoris, ischaemias and inflammatory disorders.

The present invention furthermore provides medicaments comprising the compound according to the invention, usually together with one or more inert non-toxic pharmaceutically suitable auxiliaries, and their use for the purposes mentioned above.

The compound according to the invention can act systemically and/or locally. For this purpose, it can be administered in the suitable manner, such as, for example, orally, parenterally, pulmonarily, nasally, sublingually, lingually, buccally, rectally, dermally, transdermally, conjunctivally, otically or as an implant or stent.

For these administration routes, the compound according to the invention can be administered in suitable administration forms.

Suitable for oral administration are administration forms which work according to the prior art, deliver the compound according to the invention rapidly and/or in modified form and which comprise the compound according to the invention in crystalline and/or amorphisized and/or dissolved form, such as, for example, tablets (uncoated or coated tablets, for example tablets provided with enteric coatings or coatings which dissolve in a delayed manner or are insoluble and which control the release of the compound according to the invention), tablets which rapidly disintegrate in the oral cavity or films/wafers, films/lyophilizates, capsules (for example hard or soft gelatin capsules), sugar-coated tablets, granules, pellets, powders, emulsions, suspensions, aerosols or solutions.

Parenteral administration can be carried out with avoidance of an absorption step (for example intravenously, intraarterially, intracardially, intraspinally or intralumbally) or with involvement of an absorption (for example intramuscularly, subcutaneously, intracutaneously, percutaneously or intraperitoneally). Suitable administration forms for parenteral administration are, inter alia, injection and infusion preparations in the form of solutions, suspensions, emulsions, lyophilizates or sterile powders.

Suitable for the other administration routes are, for example pharmaceutical forms for inhalation (inter alia powder inhalers, nebulizers), nasal drops, solutions or sprays, tablets to be administered lingually, sublingually or bucally, films/wafers or capsules, suppositories, aural and ophthalmic preparations, vaginal capsules, aqueous suspensions (lotions, shaker mixtures), lipophilic suspensions, ointments, creams, transdermal therapeutic systems (for example patches), milk, pastes, foams, dusting powders, implants or stents.

Preference is given to oral or parenteral administration, in particular to oral administration.

The compound according to the invention can be converted into the administration forms mentioned. This may take place in a manner known per se by mixing with inert non-toxic pharmaceutically suitable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and taste and/or odour correctants.

In general, it has been found to be advantageous to administer, in the case of parenteral administration, amounts of from about 0.001 to 1 mg/kg, preferably about 0.01 to 0.5 mg/kg, of body weight to obtain effective results. In the case of oral administration, the dosage is from about 0.01 to 100 mg/kg, preferably about 0.01 to 20 mg/kg and very particularly preferably 0.1 to 10 mg/kg, of body weight.

In spite of this, it may, if appropriate, be necessary to depart from the amounts mentioned, namely depending on the body weight, the administration route, the individual response to the active compound, the type of preparation and the time or interval at which administration takes place. Thus, in some cases, it may be sufficient to manage with less than the above-mentioned minimum amount, while in other cases the upper limit mentioned has to be exceeded. In the case of the administration of relatively large amounts, it may be advisable to divide these into a number of individual doses over the course of the day.

The following exemplary embodiments illustrate the invention. The invention is not limited to the examples.

The percentages in the tests and examples below are, unless indicated otherwise, percentages by weight; parts are parts by weight. Solvent ratios, dilution ratios and stated concentrations of liquid/liquid solutions are in each case based on volume.

A. EXAMPLES

Abbreviations and Acronyms:

CE Cholesterol ester
CETP Cholesterol ester transfer protein
DAST Dimethylaminosulphur trifluoride
DCI Direct chemical ionization (in MS)
DDQ 2,3-Dichloro-5,6-dicyano-1,4-benzoquinone
de Diastereomeric excess
DMF N,N-dimethylformamide
DMSO Dimethyl sulphoxide
EDTA Ethylenediamine-N,N,N',N'-tetraacetic acid
ee Enantiomeric excess
eq. Equivalent(s)
ESI Electrospray ionization (in MS)
h Hour(s)
HDL High density lipoprotein
HPLC High pressure, high performance liquid chromatography
LC/MS Liquid chromatography-coupled mass spectroscopy
LDL Low density lipoprotein
min Minute(s)
MS Mass spectroscopy
NMR Nuclear magnetic resonance spectroscopy
$R_t$ Retention time (in HPLC)
SPA Scintillation proximity assay
TBAF Tetrabutylammonium fluoride
TBDMSOTf tert-Butyldimethylsilyl trifluoromethanesulphonate
TFA Trifluoroacetic acid
THF Tetrahydrofuran HPLC and LC/MS Methods:

Method 1: Column: Chiralpak IA, 250 mm×4.6 mm; mobile phase: isohexane/1-propanol 97:3; flow rate: 1.0 ml/min; UV detection: 254 nm.

Method 2: Instrument: HP 1100 with DAD detection; column: Kromasil RP-18, 60 mm×2 mm, 3.5 µm; mobile phase A: 5 ml of $HClO_4$/l of water, mobile phase B: acetonitrile; gradient: 0 min 2% B→0.5 min 2% B→4.5 min 90% B→9 min 90% B; flow rate: 0.75 ml/min; temperature: 30° C.; UV detection: 210 mm.

Method 3 (LC/MS): MS instrument: Micromaβ ZQ; HPLC instrument: HP 1100 Series; UV DAD; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 mm.

Starting Materials and Intermediates: (a)

Example 1A 2-cyclopentyl-4-cyclohexyl-7,7-dimethyl-3-(4-trifluoromethylbenzoyl)-4,6,7,8-tetrahydro-1H-quinolin-5-one

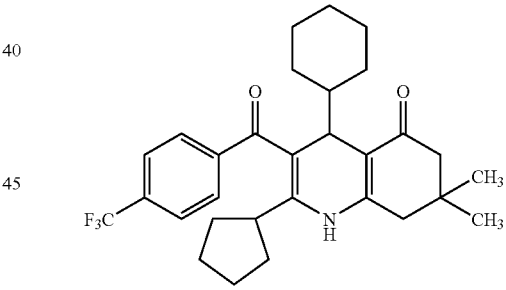

15.0 g (53 mmol, 1.2 eq.) of 3-amino-3-cyclopentyl-1-(4-trifluoromethylphenyl)propenone (preparation according to WO 03/028727, example 4) are initially charged in 500 ml of diisopropyl ether, and 6.80 ml (88 mmol, 2.0 eq.) of trifluoroacetic acid and 6.19 g (44 mmol, 1 eq.) of 5,5-dimethylcyclohexane-1,3-dione are added. After 10 min of stirring at room temperature, 7.1 ml (66 mmol, 1.5 eq.) of cyclohexanecarbaldehyde are added. The mixture is then heated under reflux on a water separator for 15 h. After cooling, the mixture is stirred in an ice bath for 30 min. The resulting precipitate is filtered off with suction and washed with cold diisopropyl ether.

Yield: 3.13 g (14% of theory)

$^1$H-NMR ($CDCl_3$, 300 MHz): δ=0.77-2.05 (m, 20H), 1.17 (s, 6H), 2.21 (m, 2H), 2.40 (2d, 2H), 3.48 (sept, 1H), 3.79 (d, 1H), 5.85 (s, 1H), 7.66 (d, 2H), 7.78 (d, 2H) ppm.

MS (ESIpos): m/z=500 [M+H]$^+$.

Example 2A 2-cyclopentyl-4-cyclohexyl-7,7-dimethyl-3-(4-trifluoromethylbenzoyl)-7,8-dihydro-6H-quinolin-5-one

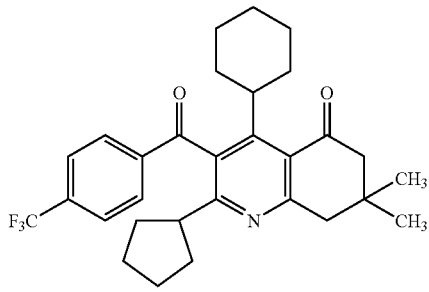

3.13 g (6.3 mmol) of the compound from Example 1A are dissolved in 64 ml of dichloromethane, and 1.42 g (6.3 mmol) of 2,3-dichloro-5,6-dicyano-1,4-benzoquinone (DDQ) are added a little at a time at 0° C. With stirring, the mixture is warmed to room temperature over a period of 3 h. The mixture is concentrated on a rotary evaporator and the residue is purified by chromatography (silica gel, mobile phase: cyclohexane/ethyl acetate 5:1).

Yield: 3.07 g (98.6% of theory)

$^1$H-NMR (CDCl$_3$, 400 MHz): δ=1.01-1.22 (m, 2H), 1.10 (s, 3H), 1.18 (s, 3H), 1.35-2.00 (m, 16H), 2.50-2.69 (m, 3H), 3.07 (s, 2H), 3.35 (m, 1H), 7.75 (d, 2H), 7.94 (m, 2H) ppm.

MS (ESIpos): m/z=498 [M+H]$^+$.

Example 3A

[(5S)-2-cyclopentyl-4-cyclohexyl-5-hydroxy-7,7-dimethyl-5,6,7,8-tetrahydroquinolin-3-yl](4-trifluoromethylphenyl)methanone

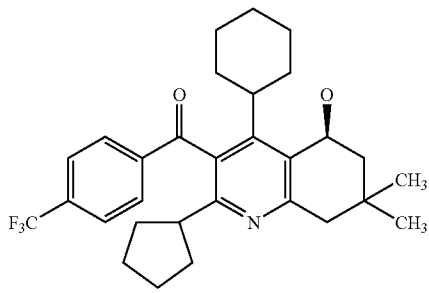

178 mg (1.2 mmol, 0.08 eq.) of (1R,2S)-1-aminoindan-2-ol are initially charged in 400 ml of THF, and 9.73 g (60 mmol, 4 eq.) of borane N,N-diethylaniline complex are added at room temperature. After the evolution of gas has ceased, the mixture is cooled to 0° C. and 7.42 g (14.9 mmol, 1 eq.) of the compound from Example 2A, dissolved in 400 ml of THF, are added. With stirring, the mixture is allowed to warm to room temperature over a period of 16 h. After the reaction has ended, 20 ml of methanol are added to the reaction mixture, the mixture is concentrated and the residue is purified by chromatography (silica gel, mobile phase: isohexane/ethyl acetate gradient).

Yield: 6.97 g (93.5% of theory)

According to method 1, the enantiomeric excess is determined as 97.6% ee.

$^1$H-NMR (CDCl$_3$, 400 MHz): δ=0.90-2.10 (m, 27H), 2.55 (m, 1H), 2.70 (m, 1H), 2.80-3.40 (m, 2H), 5.18 (br. s, 1H), 6.8 (m, 2H), 7.40-8.40 (br. m, 4H) ppm.

MS (DCI/NH$_3$): m/z=500 [M+H]$^+$.

Example 4A ((5S)-5-{[tert-butyl(dimethyl)silyl]oxy}-4-cyclohexyl-2-cyclopentyl-7,7-dimethyl-5,6,7,8-tetrahydroquinolin-3-yl)[4-(trifluoromethyl)phenyl]methanone

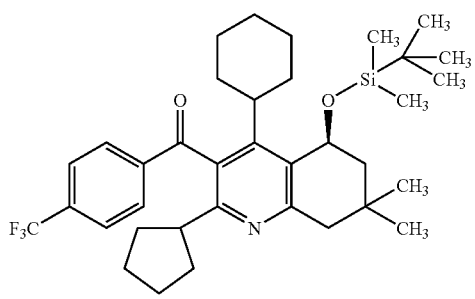

Under argon, 6.0 g (12.0 mmol) of the compound from Example 3A are initially charged in 45 ml of dry toluene. At room temperature, 5.15 g (48.0 mmol, 4 eq.) of 2,6-lutidine are then added, and the mixture is cooled to −16° C. 6.35 g (24.0 mmol, 2 eq.) of tert-butyldimethylsilyl trifluoromethanesulphonate in 15 ml of toluene are added dropwise to this solution. After 15 min, the reaction mixture is warmed to 0° C. and stirred at this temperature for 80 min. For work-up, 0.1 N hydrochloric acid (186 ml) is added and the mixture is, after warming to room temperature, extracted with ethyl acetate. The aqueous phase is re-extracted three times with ethyl acetate, the combined organic phases are washed with saturated sodium bicarbonate solution and with saturated sodium chloride solution and this aqueous phase for its part is re-extracted with ethyl acetate. The combined organic phases are dried over sodium sulphate, filtered and concentrated under reduced pressure, and the residue is purified by chromatography (silica gel, mobile phase: isohexane/ethyl acetate gradient).

Yield: 5.96 g (80.8% of theory)

$^1$H-NMR (CDCl$_3$, 300 MHz): δ=0.13 (s, 3H), 0.19 (s, 3H), 0.86 (s, 9H), 0.99-2.08 (m, 26H), 2.43-2.69 (m, 2H), 2.92-3.29 (m, 2H), 5.24 (br. s, 1H), 6.8 (m, 2H), 7.48-8.03 (br. m, 4H) ppm.

MS (DCI/NH$_3$): m/z=614 [M+H]$^+$.

Example 5A (S)-((5S)-5-{[tert-butyl(dimethyl)silyl]oxy}-4-cyclohexyl-2-cyclopentyl-7,7-dimethyl-5,6,7,8-tetrahydroquinolin-3-yl)[4-(trifluoromethyl)phenyl]methanol

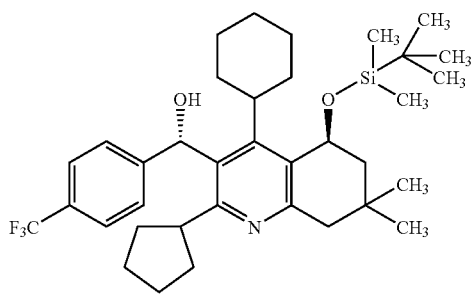

At 0° C., 10.25 ml of a 1 M solution of lithium aluminium hydride (10.25 mmol, 1.1 eq.) in THF are added dropwise to a solution of 5.72 g (9.3 mmol) of the compound from Example 4A in 116 ml of dry THF. With stirring, the mixture is warmed to room temperature over a period of 6 h. For work-up, 120 ml of a saturated sodium potassium tartrate solution are added carefully. After the evolution of gas has ceased, the mixture is extracted three times with ethyl acetate, the combined organic phases are washed with a 1:1 mixture of sodium bicarbonate solution and saturated sodium chloride solution and this aqueous phase for its part is re-extracted with ethyl acetate. The combined organic phases are dried over sodium sulphate, filtered and concentrated under reduced pressure. The residue is purified chromatographically and at the same time separated into the diastereomers of the product (column: Chiralpak AD, 500 mm×40 mm, 20 μm; mobile phase: isohexane/isopropanol 97.5:2.5; flow rate: 50 ml/min).

Yield: 2.5 g (43.6% of theory)
Diastereomeric purity: 96.9% de, $R_t$=4.15 min (method 1).
$^1$H-NMR (CDCl$_3$, 400 MHz): δ=0.18 (br. s, 6H), 0.90 (s, 9H), 1.03-2.09 (m, 26H), 2.10-2.33 (br. m, 1H), 2.37-3.06 (m, 3H), 3.33 (m, 1H), 5.24 and 5.47 (2 br. s, 1H), 6.49 and 6.64 (2 br. s, 1H), 7.31-7.64 (m, 4H) ppm.
MS (ESIpos): m/z=616 [M+H]$^+$.

Syn Diastereomer:

(R)-((5S)-5-{[tert-butyl(dimethyl)silyl]oxy}-4-cyclohexyl-2-cyclopentyl-7,7-dimethyl-5,6,7,8-tetrahydroquinolin-3-yl)[4-(trifluoromethyl)phenyl]methanol Yield: 3.56 g (61.2% of theory)
Diastereomeric purity: 98.6% de, $R_t$=2.77 min (method 1).

Example 6A (5S)-5-{[tert-butyl(dimethyl)silyl]oxy}-4-cyclohexyl-2-cyclopentyl-3-{(S)-fluoro[4-(trifluoromethyl)phenyl]methyl}-7,7-dimethyl-5,6,7,8-tetrahydroquinoline

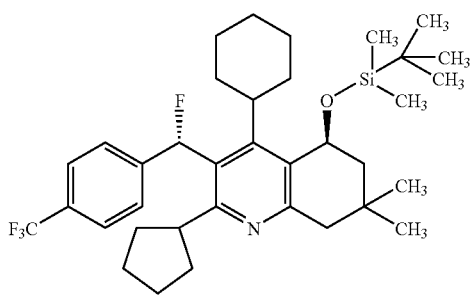

At −55° C. and under argon, 3.21 ml of diethylaminosulphur trifluoride (24.3 mmol, 1.5 eq.) are added dropwise to a solution of 9.96 g (16.2 mmol) of the compound from Example 5A in 300 ml of dry toluene. The mixture is stirred at this temperature for 1 h and then at room temperature for a further 2 h. For work-up, 120 ml of a saturated sodium bicarbonate solution are added carefully. The mixture is extracted three times in total with ethyl acetate. The combined organic phases are washed with saturated sodium chloride solution, dried over sodium sulphate, filtered and concentrated under reduced pressure. The crude product is purified by filtration through silica gel (mobile phase: cyclohexane/ethyl acetate 9:1).

Yield: 9.93 g (99.3% of theory)
$^1$H-NMR (CDCl$_3$, 400 MHz): δ=0.20 (br. s, 6H), 0.91 (s, 9H), 1.03-2.14 (m, 26H), 2.42-3.04 (m, 3H), 3.35 (m, 1H), 5.26 and 5.52 (2 br. s, 1H), 7.10-7.50 (m, 3H), 7.62 (d, 2H) ppm.
MS (ESIpos): m/z=618 [M+H]$^+$.

Working Examples (a)

Example 1

(5S)-4-cyclohexyl-2-cyclopentyl-3-{(S)-fluoro[4-(trifluoromethyl)phenyl]methyl}-7,7-dimethyl-5,6,7,8-tetrahydroquinolin-5-ol

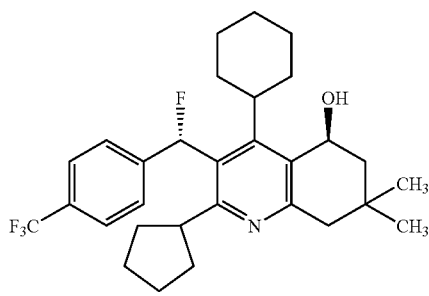

At 0° C., 40.1 ml of a 1 M solution of tetrabutylammonium fluoride (40.1 mmol, 2.5 eq.) in THF are added dropwise to a solution of 9.91 g (16.0 mmol) of the compound from Example 6A in 200 ml of dry THF. The mixture is warmed to room temperature and stirred at this temperature for 16 h. For work-up, the mixture is diluted with 100 ml of ethyl acetate and washed twice with in each case 100 ml of water and with 50 ml of saturated sodium chloride solution. The organic phase is dried over sodium sulphate, filtered and concentrated under reduced pressure. The crude product is purified chromatographically (silica gel, mobile phase: isohexane/ethyl acetate 100:0→1:1).

Yield: 7.7 g (95.3% of theory)
$^1$H-NMR (CDCl$_3$, 300 MHz): δ=1.02 (s, 3H), 1.17 (s, 3H), 1.08-2.15 (m, 21H), 2.59-3.00 (m, 3H), 3.51 (m, 1H), 5.13 (m, 1H), 7.34 (d, 2H), 7.39 (d, 1H), 7.61 (d, 2H) ppm.
MS (DCI): m/z=504 [M+H]$^+$
HPLC (method 2): $R_t$=5.20 min.

B. ASSESSMENT OF THE PHARMACOLOGICAL ACTIVITY (a)

B-I. CETP-Inhibition Testing
B-I.1. Obtainment of CETP

CETP is obtained in partially purified form from human plasma by differential centrifugation and column chromatography and used for the test. To this end, human plasma is adjusted to a density of 1.21 g per ml using NaBr and centrifuged at 4° C. at 50 000 rpm for 18 h. The bottom fraction (d>1.21 g/ml) is applied to a Sephadex® Phenyl-Sepharose 4B (Pharmacia) column, washed with 0.15 M NaCl/0.001 M tris-HCl pH 7.4 and then eluted with distilled water. The CETP-active fractions are pooled, dialysed against 50 mM sodium acetate pH 4.5 and applied to a CM-Sepharose® column (Pharmacia). The mixture is then eluted using a linear gradient (0-1 M NaCl). The pooled CETP fractions are dialysed against 10 mM tris/HCl pH 7.4 and then further purified by chromatography on a Mono Q® column (Pharmacia).

B-I.2. CETP Fluorescence Test

Measurement of the CETP-catalysed transfer of a fluorescent cholesterol ester between liposomes [modified according to the procedure of Bisgaier et al., *J. Lipid Res.* 34, 1625 (1993)]:

For the production of the donor liposomes, 1 mg of cholesteryl 4,4-difluoro-5,7-dimethyl-4-bora-3a,4a-diaza-s-indacene-3-dodecanoate (cholesteryl BODIPY® FL $C_{12}$, Molecular Probes) is dissolved in 600 μl of dioxane with 5.35 mg of triolein and 6.67 mg of phosphatidylcholine with gentle warming in an ultrasonic bath and this solution is added very slowly with ultrasonication to 63 ml of 50 mM tris/HCl, 150 mM NaCl, 2 mM EDTA buffer pH 7.3 at room temperature. The suspension is then ultrasonicated under an $N_2$ atmosphere for 30 minutes in the Branson ultrasonic bath at about 50 watts, the temperature being kept at about 20° C.

The acceptor liposomes are obtained analogously from 86 mg of cholesteryl oleate, 20 mg of triolein and 100 mg of phosphatidylcholine dissolved in 1.2 ml of dioxane and 114 ml of the above buffer by ultrasonication at 50 watts (20° C.) for 30 minutes.

B-I.2.1. CETP Fluorescence Test with Enriched CETP

For testing, a test mix consisting of 1 part of above buffer, 1 part of donor liposomes and 2 parts of acceptor liposomes is used.

50 μl of test mix are treated with 48 μl of enriched CETP fraction (1-3 μg), obtained from human plasma by means of hydrophobic chromatography, and 2 μl of a solution of the substance to be investigated in DMSO and incubated at 37° C. for 4 hours.

The change in the fluorescence at 485/535 nm is a measure of the CE transfer; the inhibition of the transfer in comparison to the control batch without substance is determined.

| Example No. | $IC_{50}$ [nM] fluorescence test |
|---|---|
| 1 | 25 |

B-I.2.2. CETP Fluorescence Test with Human Plasma

6 μl (12% v/v) of donor liposomes and 1 μl (2% v/v) of a solution of the substance to be investigated in DMSO are added to 42 μl (86% v/v) of human plasma (Sigma P9523), and the mixture is incubated at 37° C. for 24 h.

The change in the fluorescence at 510/520 nm (gap width 2.5 nm) is a measure of the CE transfer; the inhibition of the transfer in comparison to the control batch without substance is determined.

| Example No. | $IC_{50}$ [nM] fluorescence test in human plasma |
|---|---|
| 1 | 50 |

B-I.2.3. Ex Vivo-CETP Fluorescence Test

10 μl of buffer and 2 μl of serum are added to 80 μl of test mix, and the mixture is incubated at 37° C. for 4 h.

The change in the fluorescence at 485/535 nm is a measure for the CE transfer; the inhibition of the transfer is comparison to the control batch without substance is determined.

B-I.3. Obtainment of Radiolabelled HDL 50 ml of fresh human EDTA plasma is adjusted to a density of 1.12 using NaBr and centrifuged at 4° C. in a Ty 65 rotor at 50 000 rpm for 18 h. The upper phase is used for the obtainment of cold LDL. The lower phase is dialysed against 3×4 l of PDB buffer (10 mM tris/HCl pH 7.4, 0.15 mM NaCl, 1 mM EDTA, 0.02% $NaN_3$). Per 10 ml of retentate volume, 20 μl of $^3$H-cholesterol (Dupont NET-725; 1 μC/μl dissolved in ethanol) are then added and the mixture is incubated at 37° C. under $N_2$ for 72 h.

The batch is then adjusted to the density 1.21 using NaBr and centrifuged at 20° C. in a Ty 65 rotor at 50 000 rpm for 18 h. The upper phase is recovered and the lipoprotein fractions are purified by gradient centrifugation. To this end, the isolated, labelled lipoprotein fraction is adjusted to a density of 1.26 using NaBr. 4 ml each of this solution are covered in centrifuge tubes (SW 40 rotor) with 4 ml of a solution of density 1.21 and 4.5 ml of a solution of density 1.063 (density solutions of PDB buffer and NaBr) and then centrifuged for 24 h at 38 000 rpm and 20° C. in the SW 40 rotor. The intermediate layer lying between the density 1.063 and 1.21, containing the labelled HDL, is dialysed against 3×100 volumes of PDB buffer at 4° C.

The retentate contains radiolabelled $^3$H-CE-HDL, which, adjusted to about $5 \times 10^6$ cmp per ml, is used for the test.

B-I.4. CETP-SPA Test

For testing of the CETP activity, the transfer of $^3$H-cholesterol ester from human HD lipoproteins to biotinylated LD lipoproteins is measured. The reaction is ended by addition of streptavidin-SPA® beads (Amersham) and the transferred radioactivity is determined directly in a liquid scintillation counter.

In the test batch, 10 μl of HDL-3H-cholesterol ester (~50 000 cpm) are incubated at 37° C. for 18 h with 10 μl of biotin-LDL (Amersham) in 50 mM Hepes/0.15 M NaCl/0.1% bovine serum albumin/0.05% $NaN_3$ pH 7.4 containing 10 μl of CETP (1 mg/ml) and 3 μl of a solution of the substance to be tested (dissolved in 10% DMSO/1% RSA). 200 μl of the SPA-streptavidin bead solution (TRKQ 7005) are then added, incubated further with shaking for 1 h and then measured in a scintillation counter. Corresponding incubations with 10 μl of buffer, 10 μl of CETP at 4° C. and 10 μl of CETP at 37° C. serve as controls.

The activity transferred in the control batches with CETP at 37° C. is rated as 100% transfer. The substance concentration at which this transfer is reduced to half is specified as the $IC_{50}$ value.

| Example No. | $IC_{50}$ [nM] SPA Test |
|---|---|
| 1 | 7 |

B-II.1. Measurement of the Ex Vivo Activities on Transgenic hCETP Mice

To test for CETP-inhibitory activity, the substances are administered orally using a stomach tube to transgenic hCETP mice bred in-house [Dinchuk et al. BBA 1295-301 (1995)]. To this end, male animals are randomly assigned to groups having an equal number of animals, as a rule n=4, one day before the start of the experiment. Before administration of the substance, blood is taken from each mouse by puncture of the retro-orbital venous plexus for the determination of its basal CETP activity in the serum (T1). The test substance is then administered to the animals using the stomach tube. At specific times after administration of the test substance, blood is taken from the animals by puncture a second time (T2), in general 16 or 24 h after substance administration, but if appropriate this can also be carried out at another time.

In order to be able to assess the inhibitory activity of a substance, for each time, i.e. 16 or 24 hours, a corresponding control group is employed whose animals only receive the formulating agent without substance. In the control animals, the second blood sampling per animal is carried out as in the substance-treated animals in order to be able to determine the change in the CETP activity without inhibitor over the corresponding experimental time interval (16 or 24 h).

After termination of the clotting, the blood samples are centrifuged and the serum is removed by pipette. For the determination of the CETP activity, the cholesteryl ester transport over 4 h is determined. To this end, in general 2 µl of serum are employed in the test batch and the test is carried out as described under B-I.2.3.

The differences in the cholesteryl ester transport [pM CE/h (T2)−pM CE/h (T1)] are calculated for each animal and averaged in the groups. A substance which at one of the times reduces the cholesteryl ester transport by >20% is regarded as active.

| Example No. | % inhibition at 3 mg/kg | |
|---|---|---|
| | 16 h | 24 h |
| 1 | 50 | 24 |

B-II.2. Measurement of the In Vivo Activity in Syrian Golden Hamsters

Female Syrian golden hamsters bred in-house (strain BAY: DSN) and having a weight of 150-200 g are used to determine the oral action of CETP inhibitors on serum lipoproteins and triglycerides. The animals are grouped in six animals per cage and acclimatized to feed and water ad libitum for two weeks.

Immediately prior to the start of the experiment and after the substance has been administered, blood is withdrawn by retro-orbital puncture of the venous plexus and used to obtain serum after 30 min of incubation at room temperature and 20 min of centrifugation at 30 000 g. The substances are dissolved in 20% Solutol/80% water and administered per orally by means of a stomach tube. The controlled animals receive identical volumes of solvent without test substance.

Triglycerides, total cholesterol, HDL cholesterol and LDL cholesterol are determined using the analytical instrument COBAS INTEGRA 400 plus (from Roche Diagnostics) according to the instructions of the manufacturer. From the measured values, for each parameter, the change in percent caused by the treatment with the substance is calculated for each animal and stated as mean with standard deviation per group (n=6 or n=12). If, compared to the group treated with solvent, the effects of the substance are significant, the p-value determined by application of the t-test is added (* $p<0.05$;  $p<0.01$; * $p<0.005$).

| Example No. | % increase of HDL after 24 h (dose: 2 × 10 mg/kg) |
|---|---|
| 1 | 23 |

B-II.3. Measurement of the In Vivo Activity in Transgenic hCETP Mice

To determine the oral action on lipoproteins and triglycerides, test substance is administered to transgenic mice [Dinchuk et al., *BBA*, 1295-1301 (1995)] using a stomach tube. Before the start of the experiment, blood is withdrawn from the mice retro-orbitally in order to determine cholesterol and triglycerides in the serum. The serum is obtained as described above for hamsters by incubation at 4° C. overnight and subsequent centrifugation at 6000 g. After three days, blood is again withdrawn from the mice in order to determine lipoproteins and triglycerides. The changes in the parameters measured are expressed as the percentage change compared with the starting value.

| Example No. | % increase of HDL after 3 d (dose: 3 × 3 mg/kg) |
|---|---|
| 1 | 91 |

C. Working Examples Of Pharmaceutical Compositions (a)

The compound of the invention can be converted into pharmaceutical preparations in the following ways:

Tablet:
Composition:
100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:
The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99g of water.

10 ml of oral suspension correspond to a single dose of 100 mg of the compound of the invention.

Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400.20 g of oral solution correspond to a single dose of 100 mg of the compound of the invention.

Production:
The compound of the invention is suspended in the mixture of polyethylene glycol and polysorbate with stirring. The stirring process is continued until the compound of the invention has completely dissolved.

i.v. Solution:
The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

Starting Materials and Intermediates: (b)

Example 1A 4-cyclopentyl-2-isopropyl-7,7-dimethyl-3-[4-(trifluoromethyl)benzoyl]-4,6,7,8-tetrahydroquinolin-5(1H)-one

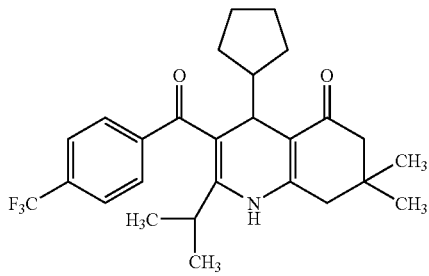

10.0 g (38.9 mmol, 1.0 eq.) of 3-amino-3-isopropyl-1-(4-trifluoromethylphenyl)propenone (preparation according to WO 03/028727, Example 2) are initially charged in 300 ml of diisopropyl ether, and 2.99 ml (38.9 mmol, 1.0 eq.) of trifluoroacetic acid and 5.45 g (38.9 mmol, 1 eq.) of 5,5-dimethylcyclohexane-1,3-dione are added. After 10 min of stirring at room temperature, the mixture is heated to reflux and 4.58 g (46.7 mmol, 1.2 eq.) of cyclopentanecarbaldehyde are added. The mixture is heated under reflux on a water separator for 15 h. After cooling, the mixture is stirred in an ice bath for 45 min and the resulting precipitate is filtered off with suction, washed with cold diisopropyl ether and freed from solvent residues under high vacuum.

Yield: 4.15 g (23% of theory)

$^1$H-NMR (CDCl$_3$, 400 MHz): δ=1.05 (d, 3H), 1.15 (s, 3H), 1.16 (s, 3H), 1.28 (d, 3H), 1.24-1.61 (m, 7H), 2.30 and 2.51 (2d, 2H), 2.34 (s, 2H), 3.49 (sept, 1H), 3.81 (d, 1H), 5.96 (s, 1H), 7.66 (d, 2H), 7.77 (d, 2H) ppm.

MS (DCI/NH$_3$): m/z=460 [M+H]$^+$, 477 [M+NH$_4$]$^+$.

Example 2A 4-cyclopentyl-2-isopropyl-7,7-dimethyl-3-[4-(trifluoromethyl)benzoyl]-7,8-dihydroquinolin-5(6H)-one

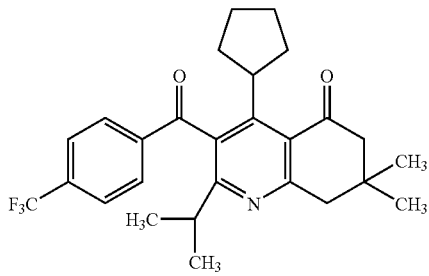

4.0 g (8.7 mmol) of the compound from Example 1A are dissolved in 100 ml of dichloro-methane, and 2.17 g (9.6 mmol, 1.1 eq.) of 2,3-dichloro-5,6-dicyano-1,4-benzoquinone (DDQ) are added a little at a time at 0° C. With stirring, the mixture is warmed to room temperature over a period of 3 h. The mixture is concentrated on a rotary evaporator and the residue is purified by chromatography (silica gel, mobile phase: isohexane/ethyl acetate 100:0→50:50).

Yield: 3.78 g (95.1% of theory)

$^1$H-NMR (CDCl$_3$, 300 MHz): δ=1.09 (d, 3H), 1.11 (s, 3H), 1.17 (s, 3H), 1.19 (d, 3H), 1.34-2.00 (m, 8H), 2.51-2.68 (m, 3H), 3.01 (m, 1H), 3.1 (s, 2H), 7.76 (d, 2H), 7.94 (m, 2H) ppm.

MS (ESIpos): m/z=458 [M+H]$^+$.

Example 3A

[(5S)-4-cyclopentyl-5-hydroxy-2-isopropyl-7,7-dimethyl-5,6,7,8-tetrahydroquinolin-3-yl][4-(trifluoromethyl)phenyl]methanone

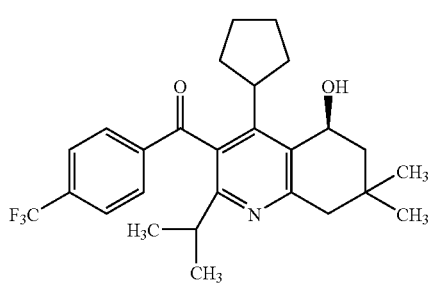

140 mg (0.96 mmol, 0.08 eq.) of (1R,2S)-1-aminoindan-2-ol are initially charged in 440 ml of THF, and 7.80 g (47.8 mmol, 4.0 eq.) of borane N,N-diethylaniline complex are added at room temperature. After the evolution of gas has ceased, the mixture is cooled to 0° C. and 5.47 g (12 mmol, 1 eq.) of the compound from Example 2A, dissolved in 40 ml of THF, are added. With stirring, the mixture is allowed to warm to room temperature over a period of 28 h. After the reaction has ended, 20 ml of methanol are added to the reaction mixture and the mixture is concentrated. The residue is partitioned between 150 ml of water and 150 ml of ethyl acetate. The aqueous phase is extracted twice with in each case 100 ml of ethyl acetate. The combined organic phases are washed with 50 ml of saturated sodium chloride solution, dried over sodium sulphate, filtered and concentrated under reduced pressure. The crude product is then purified by chromatography (silica gel, mobile phase: isohexane/ethyl acetate 4:1).

Yield: 4.97 g (90.5% of theory)

The enantiomeric excess is determined according to method 1 as being 92.5% ee.

The enantiomers are separated by chromatography on a chiral phase (column: Chiralpak AD, 500 mm×40 mm, 20 µm; mobile phase: isohexane/isopropanol 97.5:2.5; flow rate: 50 ml/min):

Yield: 4.46 g (81.2% of theory)

The enantiomeric excess is determined according to method 1 as being 98.1% ee; R$_t$ (method 1)=7.09 min.

$^1$H-NMR (CDCl$_3$, 300 MHz): δ=0.94-1.30 (m, 12H), 1.31-2.03 (m, 11H), 2.53 (m, 1H), 2.72 (d, 1H), 2.95-3.12 (m, 1H), 3.29 (m, 1H), 5.18 (m, 1H), 7.73 (d, 2H), 7.93 (m, 2H) ppm.

MS (DCI): m/z=460 [M+H]$^+$.

Example 4A ((5S)-5-{[tert-butyl(dimethyl)silyl]oxy}-4-cyclopentyl-2-isopropyl-7,7-dimethyl-5,6,7,8-tetrahydroquinolin-3-yl)[4-(trifluoromethyl)phenyl]methanone

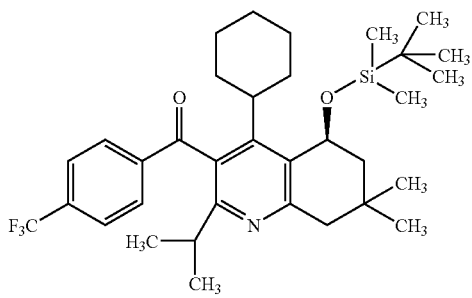

Under argon, 3.65 g (7.95 mmol) of the compound from Example 3A are initially charged in 80 ml of dry toluene. At room temperature, 3.41 g (31.8 mmol, 4 eq.) of 2,6-lutidine are then added, and the mixture is cooled to −18° C. 3.65 ml (15.9 mmol, 2 eq.) of tert-butyldimethylsilyl trifluoromethanesulphonate are added dropwise to this solution. After 20 min, the reaction mixture is warmed to 0° C. and stirred at this temperature for a further 55 min. For work-up, saturated ammonium chloride solution (100 ml) is added and the mixture is, after warming to room temperature, extracted with ethyl acetate. The aqueous phase is extracted two more times with ethyl acetate and the combined organic phases are washed with saturated sodium chloride solution, dried over sodium sulphate, filtered and concentrated under reduced pressure. The residue is purified by chromatography (silica gel, mobile phase: isohexane/ethyl acetate 9:1).

Yield: 4.65 g (quantitative)

$^1$H-NMR (CDCl$_3$, 400 MHz): δ=0.09 (s, 3H), 0.18 (s, 3H), 0.86 (s, 9H), 0.92 (s, 3H), 1.04 (d, 3H), 1.22 (d, 3H), 1.24 (s, 3H), 1.27-1.86 (m, 9H), 1.93-2.02 (m, 1H), 2.50 (m, 1H), 2.58-3.23 (m, 2H), 3.32 (m, 1H), 5.20 (m, 1H), 7.73 (d, 2H), 7.83-8.00 (m, 2H) ppm.

MS (ESIpos): m/z=574 [M+H]$^+$.

Example 5A (S)-((5S)-5-{[tert-butyl(dimethyl)silyl]oxy}-4-cyclopentyl-2-isopropyl-7,7-dimethyl-5,6,7,8-tetrahydroquinolin-3-yl)[4-(trifluoromethyl)phenyl]methanol

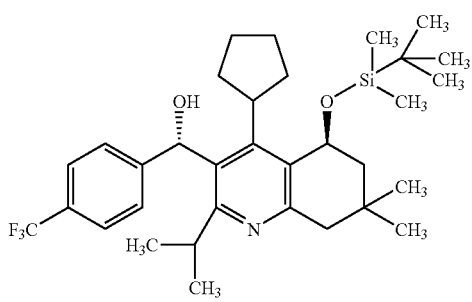

At 0° C., 12.0 ml of a 1 M solution of lithium aluminium hydride (12.0 mmol, 1.5 eq.) in THF are added dropwise to a solution of 4.59 g (8.0 mmol) of the compound from Example 4A in 80 ml of dry THF. With stirring, the mixture is warmed to room temperature over a period of 16 h. For work-up, 120 ml of a saturated sodium potassium tartrate solution are added carefully. After the evolution of gas has ceased, the mixture is extracted twice with ethyl acetate and the combined organic phases are washed with saturated sodium chloride solution, dried over sodium sulphate, filtered and concentrated under reduced pressure. The residue is purified chromatographically and at the same time separated into the diastereomers of the product (silica gel, mobile phase: isohexane/ethyl acetate 95:5).

Yield: 2.29 g (49.8% of theory)

$^1$H-NMR (CDCl$_3$, 300 MHz): δ=0.13 (s, 3H), 0.20 (s, 3H), 0.64-1.00 (m, 18H), 1.09-2.23 (m, 14H), 2.59 (d, 1H), 2.89 (m, 1H), 3.00 (m, 1H), 3.71 (m, 1H), 5.21 (t, 1H), 6.22 (br. s, 1H), 7.43 (d, 2H), 7.59 (d, 2H) ppm.

MS (ESIpos): m/z=576 [M+H]$^+$ $R_f$=0.26 (isohexane/ethyl acetate 9:1).

Syn Diastereomer:

(R)-((5S)-5-{[tert-butyl(dimethyl)silyl]oxy}-4-cyclopentyl-2-isopropyl-7,7-dimethyl-5,6,7,8-tetrahydroquinolin-3-yl)[4-(trifluoromethyl)phenyl]methanol Yield: 2.48 g (53.9% of theory)

$R_f$=0.34 (isohexane/ethyl acetate 9:1).

Example 6A (5S)-5-{[tert-butyl(dimethyl)silyl]oxy}-4-cyclopentyl-3-{(S)-fluoro[4-(trifluoromethyl)phenyl]methyl}-2-isopropyl-7,7-dimethyl-5,6,7,8-tetrahydroquinoline

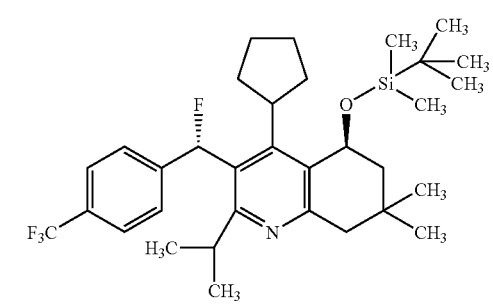

At −10° C. and under argon, 0.82 ml of diethylaminosulphur trifluoride (6.2 mmol, 1.5 eq.) is added dropwise to a solution of 2.38 g (4.1 mmol) of the compound from Example 5A in 40 ml of dry dichloromethane. The mixture is stirred at this temperature for 200 min. For work-up, 40 ml of a saturated sodium bicarbonate solution are carefully added with ice cooling. The mixture is extracted three times in total with ethyl acetate. The combined organic phases are then washed with saturated sodium chloride solution, dried over sodium sulphate, filtered and concentrated under reduced pressure. The crude product is purified by filtration through silica gel (mobile phase: cyclohexane/ethyl acetate 9:1).

Yield: 1.92 g (80.3% of theory)

LC/MS (method 3): $R_t$=3.85 min.

MS (ESIpos): m/z=578 [M+H]$^+$ $R_f$=0.66 (isohexane/ethyl acetate 9:1).

Working Examples: (b)

Example 1

(5S)-4-cyclopentyl-3-{(S)-fluoro[4-(trifluoromethyl)phenyl]methyl}-2-isopropyl-7,7-dimethyl-5,6,7,8-tetrahydroquinolin-5-ol

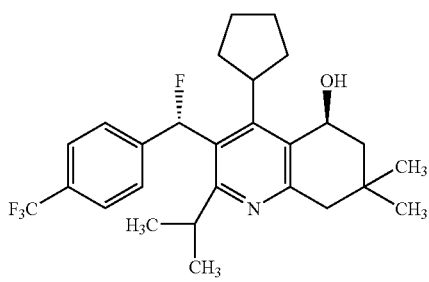

At 0° C., 13.3 ml of a 1 M solution of tetrabutylammonium fluoride (13.3 mmol, 4.0 eq.) in THF are added dropwise to a solution of 1.92 g (3.3 mmol) of the compound from Example 6A in 20 ml of dry THF. The reaction mixture is stirred in an ice bath for 4 h. For work-up, the mixture is diluted with 100 ml of ethyl acetate and washed twice with in each case 100 ml of water and with 50 ml of saturated sodium chloride solution. The organic phase is dried over sodium sulphate, filtered and concentrated under reduced pressure. The crude product is purified chromatographically (silica gel, mobile phase: isohexane/ethyl acetate 9:1→2:1).

Yield: 1.18 g (76.4% of theory)

$^1$H-NMR (CDCl$_3$, 300 MHz): δ=0.70 (d, 3H), 1.03 (s, 3H), 1.13 (d, 3H), 1.19 (s, 3H), 1.32-2.20 (m, 11H), 2.63-2.97 (m, 3H), 3.86 (m, 1H), 5.15 (m, 1H), 6.94 (d, 1H), 7.34 (d, 2H), 7.61 (d, 2H) ppm.

MS (DCI): m/z=464 [M+H]$^+$

R$_f$=0.13 (isohexane/ethyl acetate 4:1).

The further separation of diastereomers still present in the product is carried out by chromatography (column: Chiralpak AD, 500 mm×40 mm, 20 µm; mobile phase: isohexane/isopropanol 97.5:2.5; flow rate: 50 ml/min).

Yield: 0.35 g (22.9% of theory).

B. Assessment of The Pharmacological Activity (b)
B-I. CETP-Inhibition Testing
B-I.1. Obtainment of CETP CETP is obtained in partially purified form from human plasma by differential centrifugation and column chromatography and used for the test. To this end, human plasma is adjusted to a density of 1.21 g per ml using NaBr and centrifuged at 4° C. at 50 000 rpm for 18 h. The bottom fraction (d>1.21 g/ml) is applied to a Sephadex®-Phenyl-Sepharose 4B (Pharmacia) column, washed with 0.15 M NaCl/0.001 M tris/HCl pH 7.4 and then eluted with distilled water. The CETP-active fractions are pooled, dialysed against 50 mM sodium acetate pH 4.5 and applied to a CM-Sepharose column (Pharmacia). The mixture is then eluted using a linear gradient (0-1 M NaCl). The pooled CETP fractions are dialysed against 10 mM tris/HCl pH 7.4 and then further purified by chromatography on a Mono Q® column (Pharmacia).

B-I.2. CETP Fluorescence Test

Measurement of the CETP-catalysed transfer of a fluorescent cholesterol ester between liposomes [modified according to the procedure of Bisgaier et al., *J. Lipid Res.* 34, 1625 (1993)]:

For the production of the donor liposomes, 1 mg of cholesteryl 4,4-difluoro-5,7-dimethyl-4-bora-3a,4a-diaza-s-indacene-3-dodecanoate (cholesteryl BODIPY® FL C$_{12}$, Molecular Probes) is dissolved in 600 µl of dioxane with 5.35 mg of triolein and 6.67 mg of phosphatidylcholine with gentle warming in an ultrasonic bath and this solution is added very slowly with ultrasonication to 63 ml of 50 mM tris/HCl, 150 mM NaCl, 2 mM EDTA buffer pH 7.3 at room temperature. The suspension is then sonicated under an N$_2$ atmosphere for 30 minutes in the Branson ultrasonic bath at about 50 watts, the temperature being kept at about 20° C.

The acceptor liposomes are obtained analogously from 86 mg of cholesteryl oleate, 20 mg of triolein and 100 mg of phosphatidylcholine dissolved in 1.2 ml of dioxane and 114 ml of the above buffer by ultrasonication at 50 watts (20° C.) for 30 minutes.

B-I.2.1. CETP Fluorescence Test with Enriched CETP

For testing, a test mix consisting of 1 part of above buffer, 1 part of donor liposomes and 2 parts of acceptor liposomes is used.

50 µl of test mix are treated with 48 µl of enriched CETP fraction (1-3 µg), obtained from human plasma by means of hydrophobic chromatography, and 2 µl of a solution of the substance to be investigated in DMSO and incubated at 37° C. for 4 hours.

The change in the fluorescence at 485/535 m is a measure of the CE transfer; the inhibition of the transfer in comparison to the control batch without substance is determined.

| Example No. | IC$_{50}$ [nM] fluorescence test |
|---|---|
| 1 | 25 |

B-I.2.2. CETP Fluorescence Test with Human Plasma

6 µl (12% v/v) of donor liposomes and 1 µl (2% v/v) of a solution of the substance to be investigated in DMSO are added to 42 µl (86% v/v) of human plasma (Sigma P9523), and the mixture is incubated at 37° C. for 24 h.

The change in the fluorescence at 510/520 nm (gap width 2.5 nm) is a measure of the CE transfer; the inhibition of the transfer in comparison to the control batch without substance is determined.

| Example No. | IC$_{50}$ [nM] fluorescence test in human plasma |
|---|---|
| 1 | 84 |

B-I.2.3. Ex Vivo-CETP Fluorescence Test

10 µl of buffer and 2 µl of serum are added to 80 µl of test mix, and the mixture is incubated at 37° C. for 4 h.

The change in the fluorescence at 485/535 nm is a measure for the CE transfer; the inhibition of the transfer in comparison to the control batch without substance is determined.

B-I.3. Obtainment of Radiolabelled HDL 50 ml of fresh human EDTA plasma are adjusted to a density of 1.12 using NaBr and centrifuged at 4° C. in a Ty 65 rotor at 50 000 rpm for 18 h. The upper phase is used for the obtainment of cold LDL. The lower phase is dialysed against 3×4 l of PDB buffer (10 mM tris/HCl pH 7.4, 0.15 mM NaCl, 1 mM EDTA, 0.02% NaN$_3$). Per 10 ml of retentate volume, 20

μl of $^3$H-cholesterol (Dupont NET-725; 1 μC/μl dissolved in ethanol) are then added and the mixture is incubated at 37° C. under N$_2$ for 72 h.

The batch is then adjusted to the density 1.21 using NaBr and centrifuged at 20° C. in a Ty 65 rotor at 50 000 rpm for 18 h. The upper phase is recovered and the lipoprotein fractions are purified by gradient centrifugation. To this end, the isolated, labelled lipoprotein fraction is adjusted to a density of 1.26 using NaBr. 4 ml each of this solution are covered in centrifuge tubes (SW 40 rotor) with 4 ml of a solution of density 1.21 and 4.5 ml of a solution of density 1.063 (density solutions of PDB buffer and NaBr) and then centrifuged for 24 h at 38 000 rpm and 20° C. in the SW 40 rotor. The intermediate layer lying between the density 1.063 and 1.21, containing the labelled HDL, is dialysed against 3×100 volumes of PDB buffer at 4° C.

The retentate contains radiolabelled $^3$H-CE-HDL, which, adjusted to about 5×10$^6$ cmp per ml, is used for the test.

B-I.4. CETP-SPA Test

For testing of the CETP activity, the transfer of $^3$H-cholesterol ester from human HD lipoproteins to biotinylated LD lipoproteins is measured. The reaction is ended by addition of streptavidin-SPA® beads (Amersham) and the transferred radioactivity is determined directly in a liquid scintillation counter.

In the test batch, 10 μl of HDL-3H-cholesterol ester (~50 000 cpm) are incubated at 37° C. for 18 h with 10 μl of biotin-LDL (Amersham) in 50 mM Hepes/0.15 M NaCl/0.1% bovine serum albumin/0.05% NaN$_3$ pH 7.4 containing 10 μl of CETP (1 mg/ml) and 3 μl of a solution of the substance to be tested (dissolved in 10% DMSO/1% RSA). 200 μl of the SPA-streptavidin bead solution (TRKQ 7005) are then added, incubated further with shaking for 1 h and then measured in a scintillation counter. Corresponding incubations with 10 μl of buffer, 10 μl of CETP at 4° C. and 10 μl of CETP at 37° C. serve as controls.

The activity transferred in the control batches with CETP at 37° C. is rated as 100% transfer. The substance concentration at which this transfer is reduced to half is specified as the IC$_{50}$ value.

| Example No. | IC$_{50}$ [nM] SPA Test |
|---|---|
| 1 | 12 |

B-II.1. Measurement of the Ex Vivo Activities on Transgenic hCETP Mice

To test for CETP-inhibitory activity, the substances are administered orally using a stomach tube to transgenic hCETP mice bred in-house [Dinchuk et al., *BBA*, 1295-1301 (1995)]. To this end, male animals are randomly assigned to groups having an equal number of animals, as a rule n=4, one day before the start of the experiment. Before administration of the substance, blood is taken from each mouse by puncture of the retro-orbital venous plexus for the determination of its basal CETP activity in the serum (T1). The test substance is then administered to the animals using the stomach tube. At specific times after administration of the test substance, blood is taken from the animals by puncture a second time (T2), in general 16 or 24 h after substance administration, but if appropriate this can also be carried out at another time.

In order to be able to assess the inhibitory activity of a substance, for each time, i.e. 16 or 24 hours, a corresponding control group is employed whose animals only receive the formulating agent without substance. In the control animals, the second blood sampling per animal is carried out as in the substance-treated animals in order to be able to determine the change in the CETP activity without inhibitor over the corresponding experimental time interval (16 or 24 h).

After termination of the clotting, the blood samples are centrifuged and the serum is removed by pipette. For the determination of the CETP activity, the cholesteryl ester transport over 4 h is determined. To this end, in general 2 μl of serum are employed in the test batch and the test is carried out as described under B-I.2.3.

The differences in the cholesteryl ester transport [pM CE/h (T2)−pM CE/h (T1)] are calculated for each animal and averaged in the groups. A substance which at one of the times reduces the cholesteryl ester transport by >20% is regarded as active.

| Example No. | % inhibition at 3 mg/kg | |
|---|---|---|
| | 16 h | 24 h |
| 1 | 49 | 39 |

B-II.2. Measurement of the In Vivo Activity in Syrian Golden Hamsters

Female Syrian golden hamsters bred in-house (strain BAY: DSN) and having a weight of 150-200 g are used to determine the oral action of CETP inhibitors on serum lipoproteins and triglycerides. The animals are grouped in six animals per cage and acclimatized to feed and water ad libitum for two weeks.

Immediately prior to the start of the experiment and after the substance has been administered, blood is withdrawn by retro-orbital puncture of the venous plexus and used to obtain serum after 30 min of incubation at room temperature and 20 min of centrifugation at 30 000 g. The substances are dissolved in 20% Solutol/80% water and administered perorally by means of a stomach tube. The control animals receive identical volumes of solvent without test substance.

Triglycerides, total cholesterol, HDL cholesterol and LDL cholesterol are determined using the analytical instrument COBAS INTEGRA 400 plus (from Roche Diagnostics) according to the instructions of the manufacturer. From the measured values, for each parameter, the change in percent caused by the treatment with the substance is calculated for each animal and stated as mean with standard deviation per group (n=6 or n=12). If, compared to the group treated with solvent, the effects of the substance are significant, the p-value determined by application of the t-test is added (* p≦0.05;  p≦0.01; * p≦0.005).

| Example No. | % increase of HDL after 24 h (dose: 2 × 10 mg/kg) |
|---|---|
| 1 | 20 |

B-II.3. Measurement of the In Vivo Activity in Transgenic hCETP Mice

To determine the oral action on lipoproteins and triglycerides, test substance is administered to transgenic mice [Dinchuk et al., *BBA*, 1295-1301 (1995)] using a stomach tube. Before the start of the experiment, blood is withdrawn from the mice retro-orbitally in order to determine cholesterol and triglycerides in the serum. The serum is obtained as described above for hamsters by incubation at 4° C. overnight and subsequent centrifugation at 6000 g. After three days, blood is again withdrawn from the mice in order to determine lipoproteins and triglycerides. The changes in the parameters measured are expressed as the percentage change compared with the starting value.

| Example No. | % increase of HDL after 3 d (dose: 3 × 3 mg/kg) |
|---|---|
| 1 | 85 |

C. WORKING EXAMPLES OF PHARMACEUTICAL COMPOSITIONS (b)

The compounds of the invention can be converted into pharmaceutical preparations in the following ways:

Tablet:
Composition:
100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
Tablet weight 212 mg, diameter 8 mm, radius of curvature 12 mm.
Production:
The mixture of compound of the invention, lactose and starch is granulated with a 5% strength solution (m/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound of the invention.
Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring process is continued until the compound of the invention has completely dissolved.

i.v. Solution:
The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

(I)

in which R represents cyclopentyl or isopropyl, or a salt thereof.

2. A compound of the formula (Ia)

(Ia)

or a salt thereof.

3. A compound of the formula (Ib)

(Ib)

or a salt thereof.

4. A pharmaceutical composition comprising the compound of the formula (I) as defined in any of claims 1 to 3 in combination with an inert nontoxic pharmaceutically suitable auxiliary.

5. A pharmaceutical composition comprising the compound of the formula (I) as defined in any of claims 1 to 3 in combination with one or more further active compounds selected from the group consisting of antidiabetics, platelet aggregation inhibitors, anticoagulants, calcium antagonists, angiotensin AII antagonists, ACE inhibitors, beta blockers, phosphodiesterase inhibitors, stimulators of soluble guanylate cyclase, cGMP enhancers, diuretics, thyroid receptor agonists, HMG-CoA reductase inhibitors, squalene synthase inhibitors, squalene epoxidase inhibitors, oxidosqualene cyclase inhibitors, ACAT inhibitors, MTP inhibitors, PPAR agonists, fibrates, lipase inhibitors, cholesterol absorption inhibitors, bile acid reabsorption inhibitors, polymeric bile acid adsorbers and lipoprotein(a) antagonists.

6. A process for preparing the compound of the formula (Ia) as defined in claim 2, characterized in that the compound of the formula (IIa)

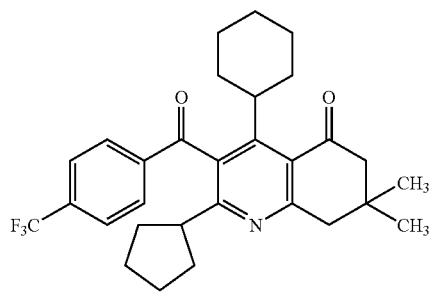
(IIa)

is initially, by asymmetric reduction, converted into the compound of the formula (IIIa)

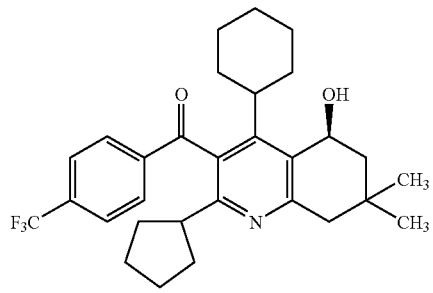
(IIIa)

which is then either

[A] by introduction of a hydroxyl protective group reacted to give a compound of the formula (IVa)

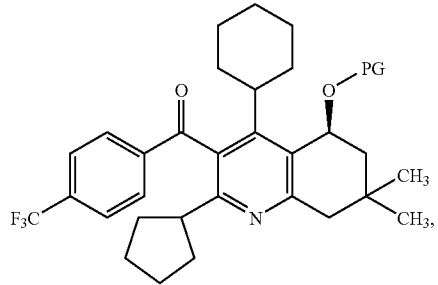
(IVa)

in which

PG represents a hydroxyl protective group, and then, by diastereoselective reduction, converted into a compound of the formula (Va)

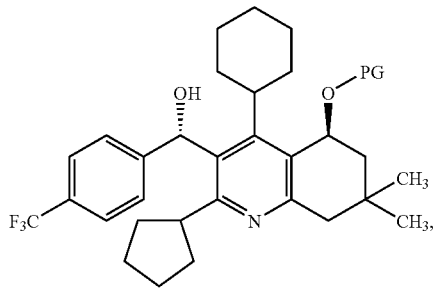
(Va)

in which PG is as defined above, or

[B] initially reduced diastereoselectively to give the compound of the formula (VIa)

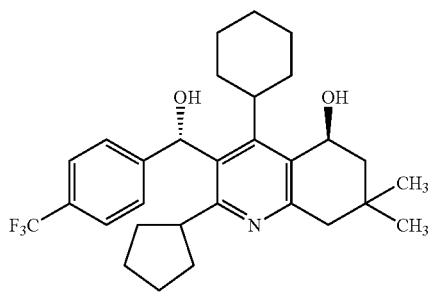
(VIa)

which is then, by regioselective introduction of the hydroxyl protective group PG, converted into a compound of the formula (Va), the compound of the formula (Va) is then, using a fluorinating agent, reacted to give a compound of the formula (VIIa)

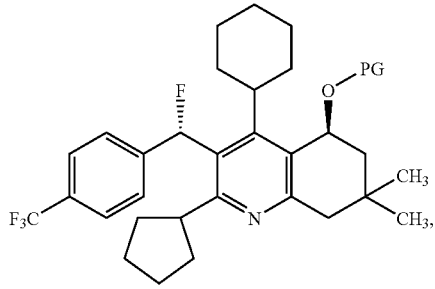
(VIIa)

in which PG is as defined above, and the hydroxyl protective group PG is then cleaved off giving the compound of the formula (Ia)

and the compound of the formula (Ia) is optionally converted into a salt thereof.

7. A process for preparing the compound of the formula (Ib) as defined in claim 3, characterized in that the compound of the formula (IIb)

(IIb)

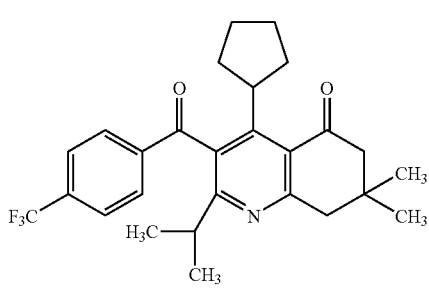

is initially, by asymmetric reduction, converted into the compound of the formula (IIIb)

(IIIb)

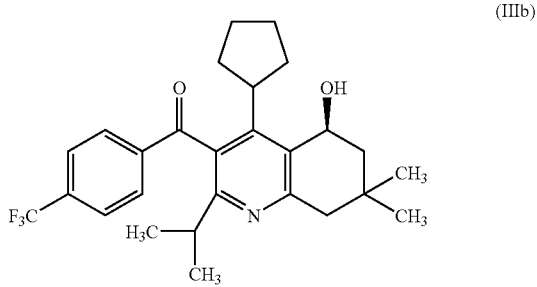

which is then either
[A] by introduction of a hydroxyl protective group reacted to give a compound of the formula (IVb)

(IVb)

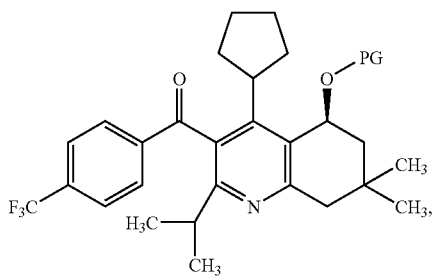

in which
PG represents a hydroxyl protective group,
and then, by diastereoselective reduction, converted into a compound of the formula (Vb)

(Vb)

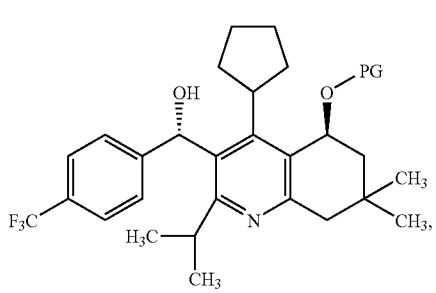

in which PG is as defined above, or
[B] initially reduced diastereoselectively to give the compound of the formula (VIb)

(VIb)

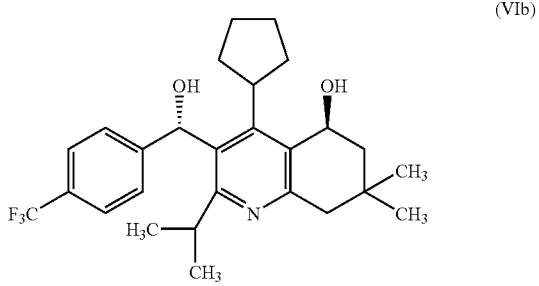

which is then, by regioselective introduction of the hydroxyl protective group PG, converted into a compound of the formula (Vb), the compound of the formula (Vb) is then, using a fluorinating agent, reacted to give a compound of the formula (VIIb)

(VIIb)

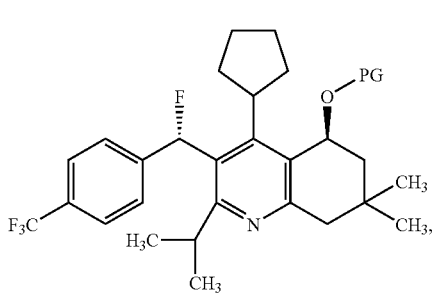

in which PG is as defined above, and the hydroxyl protective group PG is then cleaved off giving the compound of the formula (Ib)

and the compound of the formula (Ib) is optionally converted into a salt thereof.

8. The process of claim 6, wherein PG is a radical of the formula —$SiR^1R^2R^3$, in which $R^1$, $R^2$ and $R^3$ are identical or different and represent ($C_1$-$C_4$) alkyl.

9. The process of claim 7, wherein PG is a radical of the formula —$SiR^1R^2R^3$, in which $R^1$, $R^2$ and $R^3$ are identical or different and represent ($C_1$-$C_4$) alkyl.

* * * * *